US010876150B2

(12) United States Patent
Vo-Dinh et al.

(10) Patent No.: US 10,876,150 B2
(45) Date of Patent: Dec. 29, 2020

(54) NANOPROBE COMPOSITIONS AND METHODS OF USE THEREOF

(71) Applicant: Duke University, Durham, NC (US)

(72) Inventors: Tuan Vo-Dinh, Durham, NC (US); Naveen Gandra, Durham, NC (US); Hoan T. Ngo, Durham, NC (US)

(73) Assignee: Duke University, Durham, NC (US)

( * ) Notice: Subject to any disclaimer, the term of this patent is extended or adjusted under 35 U.S.C. 154(b) by 235 days.

(21) Appl. No.: 15/882,380

(22) Filed: Jan. 29, 2018

(65) Prior Publication Data

US 2018/0230523 A1 Aug. 16, 2018

Related U.S. Application Data

(60) Provisional application No. 62/451,106, filed on Jan. 27, 2017.

(51) Int. Cl.
*B82Y 15/00* (2011.01)
*C12Q 1/6825* (2018.01)
(Continued)

(52) U.S. Cl.
CPC .......... *C12Q 1/6825* (2013.01); *A61B 5/0075* (2013.01); *B82Y 20/00* (2013.01); *G01N 21/658* (2013.01); *B82Y 15/00* (2013.01); *B82Y 30/00* (2013.01); *C12Q 2565/518* (2013.01); *C12Q 2565/549* (2013.01); *C12Q 2565/632* (2013.01)

(58) Field of Classification Search
None
See application file for complete search history.

(56) References Cited

U.S. PATENT DOCUMENTS

| 2005/0056118 A1* | 3/2005 | Xia | B22F 1/0007 75/330 |
| 2011/0215277 A1* | 9/2011 | Khan | B01J 8/00 252/408.1 |

(Continued)

OTHER PUBLICATIONS

Sun et al, Adv. Mater., vol. 15, pp. 641-646, published Apr. 9, 2003.*

(Continued)

*Primary Examiner* — Robert T Crow
(74) *Attorney, Agent, or Firm* — NK Patent Law

(57) ABSTRACT

Gold nanorattle probes are provided that are highly tunable, physiologically stable, and ultra-bright Raman probes for in vitro and in vivo surface-enhanced Raman scattering (SERS) applications. The nanorattles contain an essentially uniform gap between core and shell that is tunable and can range from 2 nm to 10 nm in width. This provides numerous advantages including allowing for increased loading with a variety of dye molecules that exhibit SERS in various spectral regions, including the "tissue optical window" for in vivo studies. In addition, the nanorattle probes provide an internal label when used in diagnostic methods to detect nucleic acids, proteins and other biotargets. The nanorattles have an essentially spherical gold metal nanoparticle core, a porous material of silver metal of an essentially uniform width surrounding the nanoparticle core that is loaded with one or more SERS reporter molecules, and an outer gold metal shell encapsulating the porous material.

16 Claims, 19 Drawing Sheets

(51) Int. Cl.
  A61B 5/00    (2006.01)
  B82Y 20/00   (2011.01)
  G01N 21/65   (2006.01)
  B82Y 30/00   (2011.01)

(56) References Cited

U.S. PATENT DOCUMENTS

2014/0127305 A1* 5/2014 Ortac .................. A61K 9/5115
                                                  424/490
2014/0241992 A1* 8/2014 Yeh ................... A61K 41/0052
                                                  424/9.6

OTHER PUBLICATIONS

Schatz, G.C., Van Duyne, R.P., "Electromagnetic Mechanism of Surface-Enhanced Spectroscopy", Reproduced from: Handbook of Vibrational Spectroscopy, 2006, 16 pgs. John Wiley & Sons, Ltd, Chichester, 2002.
T. Vo-Dinh, M.Y.K. Hiromoto, G. M. Begun, R. L Moody, "Surface-Enhanced Raman Spectroscopy for Trace Organic Analysis", Analytical Chemistry, 1984, pp. 1667-1670, vol. 56.
M. M. Kerker, "Electromagnetic Model for Surface-Enhanced Raman Scattering (SERS) on Metal Colloids", Accounts of Chemical Research, Aug. 1984, pp. 271-277, vol. 17(8).
K. Kneipp, H. Kneipp, I. Itzkan, R. R Dasar, M. S. Feld, "Surface-Enhanced Raman Scattering and Biophysics", Journal of Physics: Condensed Matter, 2002, Matter 14, R597.
T. Vo-Dinh, et al., "Plasmonic Nanoprobes: From Chemical Sensing to Medical Diagnostics and Therapy", Nanoscale, 2013, pp. 10127-10140, vol. 5 (21).
Steel, A. B., et al., "Electrochemical Quantitation of DNA Immobilized on Gold", Analytical Chemistry, 1998, pp. 4670-4677, vol. 70 (22).
Herne, T. M., Tarlov, M. J., "Characterization of DNA Probes Immobilized on Gold Surfaces", Journal American Chemical Society, Jun. 13, 1997, pp. 8916-8920, vol. 119 (38).
Burges, J. D., Hawkridge, F. M., "Octadecyl Mercaptan Submonolayers on Silver Electrodeposited on Gold Quartz Crystal Microbalance Electrodes", Langmuir, 1997, pp. 3781-3786, vol. 13.
Alvarez-Puebla, R. A., Liz-Marzan, L. M., "SERS-Based Diagnosis and Biodetection", Small, Mar. 8, 2010, pp. 604-610, vol. 6, No. 5.
J. V. Jokerst, et al., "Gold Nanorods for Ovarian Cancer Detection with Photoacoustic Imaging and Resection Guidance via Raman Imaging in Living Mice" Acs Nano, 2012, pp. 10366-10377, vol. 6, No. 11.
S. Keren, et al., "Noninvasive Molecular Imaging of Small Living Subjects Using Raman Spectroscopy" Proceedings National Academy of Sciences of the USA, Apr. 15, 2008, pp. 5844-5849, vol. 105, No. 15.
P. Dey, W. Olds, I. Blakey, K. J. Thurecht, E. L. Izake, P. M. Fredericks, "SERS-Based Detection of Barcoded Gold Nanoparticle Assemblies From Within Animal Tissue", Journal of Raman Spectroscopy, 2013, pp. 1659-1665, vol. 44.
N. Gandra, S. Singamaneni, "Surface-enhanced Raman Scattering for in vivo Imaging: the Future Looks BRIGHT", Nanomedicine, 2013, pp. 317-320, vol. 8(3).
Z. A. Nima, A. Biswas, I. S. Bayer, F. D. Hardcastle, D. Perry, A. Ghosh, E. Dervishi, A. S. Biris, "Applications of Surface-Enhanced Raman Scattering in Advanced Bio-Medical Technologies and Diagnostics", Drug Metabolism Reviews, 2014, pp. 155-175, vol. 46(2).
B. Sharma, K. Ma, M. R. Glucksberg, R. P. Van Duyne, "Seeing through Bone with Surface-Enhanced Spatially Offset Raman Spectroscopy", Journal American Chemical Society, 2013, pp. 17290-17293, vol. 135.
C. L. Zavaleta, et al., "Multiplexed Imaging of Surface Enhanced Raman Scattering Nanotags in Living Mice Using Noninvasive Raman Spectroscopy" Proceedings National Academy of Sciences of the USA, Aug. 11, 2009, pp. 13511-13516, vol. 106, No. 32.

N. Gandra, C. Portz, S. Singamaneni, "Multifunctional Plasmonic Nanorattles for Spectrum-Guided Locoregional Therapy", Advanced Materials, 2014, pp. 424-429, vol. 26.
L. Tian, N. Gandra, S. Singamaneni, Monitoring Controlled Release of Payload from Gold Nanocages Using Surface Enhanced Raman Scattering, ACS Nano, 2013, pp. 4252-4260, vol. 7, No. 5.
T. Vo-Dinh, "Surface-Enhanced Raman Spectroscopy Using Metallic Nanostructures", TrAC, Trends, Analytical Chemistry, 1998, pp. 557582, vol. 17.
H. Kang, et al., "Near-Infrared SERS Nanoprobes with Plasmonic Au/Ag Hollow-Shell Assemblies for In Vivo Multiplex Detection", Advanced Functional Materials, 2013, pp. 3719-3727, vol. 23.
A. M. Goodman, Y. Cao, C. Urban, O. Neumann, C. Ayala-Orozco, M. W. Knight, A. Joshi, P. Nordlander, N. J. Halas, "The Surprising in Vivo Instability of Near-IR-Absorbing Hollow Au—Ag Nanoshells", ACS Nano, Apr. 22, 2014, pp. 3222-3231, vol. 8, No. 4.
X. Qian, X.-H. Peng, D. O. Ansari, Q. Yin-Goen, G. Z. Chen, D. M. Shin, L. Yang, A. N. Young, M. D. Wang, S. Nie, "In Vivo Tumor Targeting and Spectroscopic Detection With Surface-Enhanced Raman Nanoparticle Tags", Nature Biotechnology, Jan. 26, 2008, pp. 83090, vol. 26, No. 1.
H. Yuan, A. M. Fales, C. G. Khoury, J. Liu, T. Vo-Dinh, J. Raman, "Spectral Characterization and Intracellular Detection of Surface-Enhanced Raman Scattering (SERS)-Encoded Plasmonic Gold Nanostars", Journal Raman Spectroscopy, 2013, pp. 234-239, vol. 44.
N. Gandra, S. Singamaneni, "Bilayered Raman-Intense Gold Nanostructures With Hidden Tags (Brights) for High-Resolution Bioimaging", Advanced Materials, Feb. 20, 2013, pp. 1022-1027, vol. 25(7).
D. K. Lim, K.-S. Jeon, J.-H. Hwang, H. Kim, S. Kwon, Y. D. Suh, J.-M. Nam, "Highly Uniform and Reproducible Surface-Enhanced Raman Scattering From DNA-Tailorable Nanoparticles With 1-Nm Interior Gap", Nature Nanotechnology, May 29, 2011, pp. 452-460, vol. 6(7).
J. Song, B. Duan, C. Wang, J. Zhou, L Pu, Z. Fang, P. Wang, T. T. Lim, H. Duan, SERS-Encoded Nanogapped Plasmonic Nanoparticles: Growth of Metallic Nanoshell by Templating Redox-Active Polymer Brushes, Journal American Chemical Society, May 14, 2014, pp. 6838-6841, vol. 136(19).
B. Y. Zhao, J. Shen, S. Chen, D. Wang, F. Li, S. Mathur, S. Song, C. Fan, "Gold Nanostructures Encoded by Non-Fluorescent Small Molecules in Polya-Mediated Nanogaps as Universal SERS Nanotags for Recognizing Various Bioactive Molecules", Chemical Science, 2014, pp. 4460-4466, vol. 5.
J. Chen, F. Saeki, B. J. Wiley, H. Cang, M. J. Cobb, Z.-Y. Li, L. Au, H. Zhang, M. B. Kimmey, Li, Y. Xia, "Gold Nanocages: Bioconjugation and Their Potential Use as Optical Imaging Contrast Agents", Nano Letters, 2005, pp. 473-477, vol. 5, No. 3.
S. E. Skrabalak, J. Chen, Y. Sun, X. Lu, L. Au, C. M. Cobley, Y. Xia, "Gold Nanocages: Synthesis, Properties, and Applications", Accounts of Chemical Research, Dec. 2008, pp. 1587-1595, vol. 41, No. 12.
X. Xia, Y. Wang, A. Ruditskiy, Y. Xia, "25th Anniversary Article: Galvanic Replacement: A Simple and Versatile Route to Hollow Nanostructures With Tunable and Well-Controlled Properties", Advanced Materials, Nov. 26, 2013, pp. 6313-6333, vol. 25(44).
S. W. Choi, Y. Zhang, Y. Xia, "A Temperature-Sensitive Drug Release System Based on Phase-Change Materials", Angew. Chem. Int. Ed., Oct. 18, 2010, pp. 7904-7908, vol. 49(43).
G. D. Moon, S. W. Choi, X. Cai, W. Li, E. C. Cho, U. Jeong, L V. Wang, Y. Xia, "A New Theranostic System Based on Gold Nanocages and Phase-Change Materials With Unique Features for Photoacoustic Imaging and Controlled Release", Journal American Chemical Society, Apr. 6, 2011, pp. 4762-4765, vol. 133(13).
G. M. Palmer, A. N. Fontanella, S. Shan, G. Hanna, G. Zhang, C. L. Fraser, M. W. Dewhirst, In Vivo Optical Molecular Imaging and Analysis in Mice Using Dorsal Window Chamber Models Applied to Hypoxia, Vasculature and Fluorescent Reporters, Nature Protocols, Aug. 18, 2011, pp. 1355-1366, vol. 6, No. 9.
H. Yuan, C. G. Khoury, H. Hwang, C. M. Wilson, G. A. Grant, T. Vo-Dinh, "Gold Nanostars: Surfactant-Free Synthesis, 3D Modelling, and Two-Photon Photoluminescence Imaging", Nanotechnology, Feb. 24, 2012, pp. 075102, vol. 23(7).

(56) References Cited

OTHER PUBLICATIONS

N. Gandra, A. Abbas, L. Tian, S. Singamaneni, "Plasmonic Planet—Satellite Analogues: Hierarchical Self-Assembly of Gold Nanostructures", Nano Letters, 2012, pp. 2645-2651, vol. 12(5).
Ariey, F., et al., A Molecular Marker of Artemisinin-Resistant Plasmodium Falciparum Malaria, Nature, Jan. 2, 2014, pp. 50-55, vol. 505(7481).
Bessetti, J., "An Introduction to PCR Inhibitors", Profiles in DNA, Mar. 2007, pp. 9-10, vol. 10(1).
Cao, Y.W.C., Jin, R.C., Mirkin, C.A., 2002, Nanoparticles With Raman Spectroscopic Fingerprints for DNA and RNA Detection, Science, Aug. 30, 2002, pp. 1536-1540, vol. 297(5586).
Chen, H.M., Liu, R.S., Asakura, K., Lee, J.F., Jang, L.Y., Hu, S.F., "Fabrication of Nanorattles With Passive Shell", 2006, J. Phys. Chem. B, pp. 19162-19167, vol. 110(39).
Chen, Z., Yu, D., Huang, Y., Zhang, Z., Liu, T., Zhan J., "Tunable SERS-Tags-Hidden Gold Nanorattles for Theranosis of CancerCells with Single Laser Beam", 2014, Scientific Reports, vol. 4:6709.
Doering, W.E., Nie, S., Spectroscopic Tags Using Dye-Embedded Nanoparticles and Surface-Enhanced Raman Scattering, Analytical Chemistry, Nov. 15, 2003, pp. 6171-6176, 75, No. 22.
Dondorp, A.M., et al., "Artemisinin Resistance in Plasmodium Falciparum Malaria", New England Journal of Medicine, Jul. 30, 2009, pp. 455-467, vol. 361(5).
Donnelly, T., Smith, W.E., Faulds, K., Graham, D., "Silver and Magnetic Nanoparticles for Sensitive DNA Detection by SERS ", Chemical Communincations, 2014, pp. 12907-12910, vol. 50(85).
Fabris, L., Dante, M., Braun, G., Lee, S.J., Reich, N.O., Moskovits, M., Nguyen, T.Q., Bazan, G.C., "A Heterogeneous PNA-Based SERS Method for DNA Detection", Journal American Chemical Society, May 16, 2007, pp. 6086-6087, vol. 129(19).
Faulds, K., Barbagallo, R.P., Keer, J.T., Smith, W.E, Graham, D., "Serrs as a More Sensitive Technique for the Detection of Labelled Oligonucleotides Compared to Fluorescence", Analyst, 2004, pp. 567-568, vol. 129(7).
Faulds, K., Jarvis, R., Smith, W.E., Graham, D., Goodacre, R., Multiplexed Detection of Six Labelled Oligonucleotides Using Surface Enhanced Resonance Raman Scattering (SERRS), Analyst 2008, pp. 1505-1512, vol. 133(11).
Feng, Y.H., Wang, Y., Wang, H., Chen, T., Tay, Y.Y., Yao, L., Yan, Q.Y., Li, S.Z., Chen, H.Y., "Engineering "Hot" Nanoparticles for Surface-Enhanced Raman Scattering by Embedding Reporter Molecules in Metal Layers", Small, Jan. 23, 2012, pp. 246-251 vol. 8(2).
Gandra, N., Singamaneni, S., Bilayered Raman-Intense Gold Nanostructures With Hidden Tags (Brights) for High-Resolution Bioimaging, Advanced Materials, Feb. 20, 2013, pp. 1022-1027 25(7).
Gao, F.L., Lei, J.P., Ju, H.X., "Label-Free Surface-Enhanced Raman Spectroscopy for Sensitive DNA Detection by DNA-Mediated Silver Nanoparticle Growth", Analytical Chemistry, Dec. 17, 2013, pp. 11788-11793, vol. 85(24).
He, Y., Su, S., Xu, T.T., Zhong, Y.L., Zapien, J.A., Li, J., Fan, C.H., Lee, S.T., 2011, Nano Today 6(2), 122-130.
Jaiswal, A., Tian, L.M., Tadepalli, S., Liu, K.K., Fei, M., Farrell, M.E., Pellegrino, P.M., Singamaneni, S., Plasmonic Nanorattles With Intrinsic Electromagnetic Hot-Spots for Surface Enhanced Raman Scattering, Small, Nov. 12 2014, pp. 4287-4292, vol. 10(21).
Jiang, Z.Y., Jiang, X.X., Su, S., Wei, X.P., Lee, S.T., He, Y., "Silicon-Based Reproducible and Active Surface Enhanced Raman Scattering Substrates for Sensitive, Specific, and Multiplex DNA Detection", Applied Physical Letters, 2012, pp. 203104-1-203104-4, vol. 100(20).
Johnson, R.P., Richardson, J.A., Brown, T., Bartlett, P.N., A Label-Free, Electrochemical SERS-Based Assay for Detection of DNA Hybridization and Discrimination of Mutations, Aug. 29, 2012, Journal American Chemical Society, pp. 14099-14107, vol. 134(34).
Kang, T., Yoo, S.M., Yoon, I., Lee, S.Y., Kim, B., Patterned Multiplex Pathogen DNA Detection by Au Particle-On-Wire SERS Sensor, Nano Letters, Apr. 14, 2010, pp. 1189-1193, vol. 10(4).

Khalavka, Y., Becker, J., Sonnichsen, C., "Synthesis of Rod-Shaped Gold Nanorattles With Improved Plasmon Sensitivity and Catalytic Activity", Journal American Chemical Society, 2009, pp. 1871-1875, vol. 131(5).
Kneipp, K., Wang, Y., Kneipp, H., Perelman, L.T., Itzkan, I., Dasari, R., Feld, M.S., "Single Molecule Detection Using Surface-Enhanced Raman Scattering (SERS)", Physical Review Letters, Mar. 3, 1997, pp. 1667-1670, vol. 78(9).
Kustner, B., Gellner, M., Schutz, M., Schoppler, F., Marx, A., Strobel, P., Adam, P., Schmuck, C., Schlücker, S., "SERS Labels for Red Laser Excitation: Silica-Encapsulated Sams on Tunable Gold/Silver Nanoshells", Angew. Chem. Int. Edit., 2009, pp. 1950-1953, vol. 48(11).
Lane, L.A., Qian, X.M., Nie, S.M., "SERS Nanoparticles in Medicine: From Label-Free Detection to Spectroscopic Tagging", Chemical Reviews, 2015, pp. 10489-10529, vol. 115(19).
Lee, S., Chon, H., Lee, J., Ko, J., Chung, B.H., Lim, D.W., Choo, J., "Rapid and Sensitive Phenotypic Marker Detection on Breast Cancer Cells Using Surface-Enhanced Raman Scattering (SERS) Imaging", Biosensors and Bioelectronics, Jan. 15, 2014, pp. 238-243, vol. 51.
Lee, S., Chon, H., Yoon, S.Y., Lee, E.K., Chang, S.I., Lim, D.W., Choo, J., "Fabrication of SERS-Fluorescence Dual Modal Nanoprobes and Application to Multiplex Cancer Cell Imaging", Nanoscale, Jan. 7, 2012, pp. 124-129, vol. 4(1).
Li, J.F., Huang, Y.F., Ding, Y., Yang, Z.L., Li, S.B., Zhou, X.S., Fan, F.R., Zhang, W., Zhou, Z.Y., WuDe, Y., Ren, B., Wang, Z.L., Tian, Z.Q., Shell-Isolated Nanoparticle-Enhanced Raman Spectroscopy, Nature, Mar. 18, 2010, pp. 392-395, vol. 464(7287).
Li, J.M., Ma, W.F., You, L.J., Guo, J., Hu, J., Wang, C.C., "Highly Sensitive Detection of Target ssDNA Based on SERS Liquid Chip Using Suspended Magnetic Nanospheres as Capturing Substrates", Langmuir, May 21, 2013, pp. 6147-6155, vol. 29(20).
Li, J.M., Wei, C., Ma, W.F., An, Q., Guo, J., Hu, J., Wang, C.C., "Multiplexed SERS Detection of DNA Targets in a Sandwich-Hhybridization Assay Using SERS-encoded Core-Shell Nanospheres", J Mater Chem, 2012, pp. 12100-12106, vol. 22(24).
Li, M., Cushing, S.K., Liang, H.Y., Suri, S., Ma, D.L., Wu, N.Q., "Plasmonic Nanorice Antenna on Triangle Nanoarray for Surface-Enhanced Raman Scattering Detection of Hepatitis B Virus DNA", Analytical Chemistry, Feb. 19, 2013, pp. 2072-2078, vol. 85(4).
Lim, D.K., Jeon, K.S., Hwang, J.H., Kim, H., Kwon, S., Suh, Y.D., Nam, J.M., "Highly Uniform and Reproducible Surface-Enhanced Raman Scattering From DNA-Tailorable Nanoparticles With 1-Nm Interior Gap", Nature Nanotechnology, May 29, 2011, pp. 452-460, vol. 6(7).
Liu, K.-K., Tadepalli, S., Tian, L., Singamaneni, S., "Size-Dependent Surface Enhanced Raman Scattering Activity of Plasmonic Nanorattles", 2015, Chemitry of Materials, pp. 5261-5270, vol. 27(15).
Liu X., Knauer, M., Ivleva, N.P., Niessner, R., Haisch, C., "Synthesis of Core-Shell Surface-Enhanced Raman Tags for Bioimaging", Analytical Chemistry, Jan. 1, 2010, pp. 441-446, vol. 82(1).
Luo Z., Chen, K., Lu, D., Han, H., Zou, M., "Synthesis of P-Aminothiophenol-Embedded Gold/Silver Core-Shell Nanostructures as Novel SERS Tags for Biosensing Applications", 2011. Microchim. Acta 173(1-2), 149-156.
Mayr, R., Haider, M., Thünauer, R., Haselgrübler, T., Schütz, G.J., Sonnleitner, A., Hesse, J., "A Microfluidic Platform for Transcription- and Amplification-Free Detection of Zepto-Mole Amounts of Nucleic Acid Molecules", Biosensors and Bioelectronics, Apr. 15, 2016, pp. 1-6, vol. 78.
Mir-Simon, B., Reche-Perez, I., Guerrini, L., Pazos-Perez, N., Alvarez-Puebla, R.A., "Universal One-Pot and Scalable Synthesis of SERS Encoded Nanoparticles", 2015, Chemistry of Materials, pp. 950-958, vol. 27(3).
Mohon, A., Alam, M.S., Bayih, A.G., Folefoc, A., Shahinas, D., Haque, R., Pillai, D.R., "Mutations in Plasmodium Falciparum K13 Propeller Gene From Bangladesh (2009-2013)", Malaria Journal, Nov. 18, 2014, pp. 413-419 vol. 13.
Ngo, H., Wang, H.-N., Burke, T., Ginsburg, G., Vo-Dinh, T., "Multiplex Detection of Disease Biomarkers Using SERS Molecu-

(56) References Cited

OTHER PUBLICATIONS lar Sentinel-On-Chip", Analytical and Bioanalytical Chemistry, May 2014, pp. 3335-3344, vol. 406(14).
NGO, H.T., Wang, H.N., Fales, A.M., Nicholson, B.P., Woods, C.W., Vo-Dinh, T., DNA Bioassay-On-Chip Using SERS Detection for Dengue Diagnosis, Analyst, Nov. 21, 2014, , pp. 5655-5659, vol. 139(22).
Ngo, H.T., Wang, H.N., Fales, A.M., Vo-Dinh, T., "Label-Free DNA Biosensor Based on SERS Molecular Sentinel on Nanowave Chip", Analytical Chemistry, Jul. 2, 2013, pp. 6378-6383, vol. 85(13).
Nie, Shumig, Emory, S.R., "Probing Single Molecules and Single Nanoparticles by Surface-Enhanced Raman Scattering", Science, Feb. 21, 1997, pp. 1102-1106, vol. 275.
Niemz, A., Ferguson, T.M., Boyle, D.S., "Point-Of-Care Nucleic Acid Testing for Infectious Diseases", Trends Biotechnology, May 2011, pp. 240-250, vol. 29(5).
Noedl, H., Se, Y., Schaecher, K., Smith, B.L., Socheat, D., Fukuda, M.M., Consortium, A.S., Evidence of Artemisinin-Resistant Malaria in Western Cambodia, New England Journal of Medicine , Dec. 11, 2008, pp. 2619-2620, vol. 359(24).
Papadopoulou, E., Bell, S.E.J., "Label-Free Detection of Single-Base Mismatches in DNA by Surface-Enhanced Raman Spectroscopy", Angewandte Chemie International Edition, Sep. 19, 2011, pp. 9058-9061, vol. 50(39).
Qi, J., Zeng, J., Zhao, F., Lin, S.H., Raja, B., Strych, U., Willson, R.C., Shih, W.C., "Label-Free, In Situ SERS Monitoring of Individual DNA Hybridization in Microfluidics", Nanoscale, Aug. 7, 2014, pp. 8521-8526, vol. 6(15).
Schlucker, S., 2014, "Surface-Enhanced Raman Spectroscopy: Concepts and Chemical Applications", Angewandte Chemie International Edition, 2014, pp. 4756-4795, vol. 53(19).
Sha, M.Y., Xu, H., Natan, M.J., Cromer, R., "Surface-Enhanced Raman Scattering Tags for Rapid and Homogeneous Detection of Circulating Tumor Cells in the Presence of Human Whole Blood", 2008, Journal American Chemical Society, pp. 17214-17215, vol. 130(51).
Song, J., Duan, B., Wang, C., Zhou, J., Pu, L, Fang, Z., Wang, P., Lim, T.T., Duan, H., "SERS-Encoded Nanogapped Plasmonic Nanoparticles: Growth of Metallic Nanoshell by Templating Redox-Active Polymer Brushes", Journal American Chemical Society, 2014, pp. 6838-6841, vol. 136(19).
Sun, L., Yu, C.X., Irudayaraj, J., "Surface-Enhanced Raman Scattering Based Nonfluorescent Probe for Multiplex DNA Detection", Analytical Chemistry, Jun. 1, 2007, pp. 3981-3988, vol. 79(11).
Sun, Y.G., Wiley, B., Li, Z.Y., Xia, Y.N., "Synthesis and Optical Properties of Nanorattles and Multiple-Walled Nanoshells/ Nanotubes Made of Metal Alloys", Journal American Chemical Society, 2004, pp. 9399-9406, vol. 126(30).
Vo-Dinh, T., "Surface-Enhanced Raman Spectroscopy Using Metallic Nanostructures", Trac-Trend, Analytical Chemistry, 1998, pp. 557-582, vol. 17(8-9).
Vo-Dinh, T., Dhawan, A., Norton, S.J., Khoury, C.G., Wang, H.N., Misra, V., Gerhold, M.D., "Plasmonic Nanoparticles and Nanowires: Design, Fabrication and Application in Sensing", Journal Phys. Chem. C Nanomater Interfaces, Apr. 29, 2010, pp. 7480-7488, vol. 114(16).
Wei, X.P., Su, S., Guo, Y.Y., Jiang, X.X., Zhong, Y.L, Su, Y.Y., Fan, C.H., Lee, S.T., He, Y., "A Molecular Beacon-Based Signal-Off Surface-Enhanced Raman Scattering Strategy for Highly Sensitive, Reproducible, and Multiplexed DNA Detection", Small, 2013, pp. 2493-2499, vol. 9, No. 15.
Mahajan, S., Richardson, J., Brown, T., Bartlett, P.N., "SERS-Melting: A New Method for Discriminating Mutations in DNA Sequences", 2008, Journal American Chemical Society, 130(46), 15589-15601.
Xu, H., Sha, M., Cromer, R., Penn, S., Holland, E., Chakarova, G., Natan, M., 2012, Portable SERS Sensor for Sensitive Detection of Food-Borne Pathogens. In: Kumar, C.S.R. (Ed.), Raman Spectroscopy for Nanomaterials characterization, pp. 531-551. Springer Berlin Heidelberg.
Xu, H.X., "Multilayered Metal Core-Shell Nanostructures for Inducing a Large and Tunable Local Optical Field", Physical Review B, 2005, pp. 073405-1-073405-4, vol. 72(7).
Xu, L.J., Lei, Z.C., Li, J.X., Zong, C., Yang, C.J., Ren, B., "Label-Free Surface-Enhanced Raman Spectroscopy Detection of DNA With Single-Base Sensitivity", Journal American Chemical Society, Apr. 2, 2015, pp. 5149-5154, vol. 137(15).
Xu, S., Zhao, B., Xu, W., Fan, Y., "Preparation of Au—Ag Coreshell Nanoparticles and Application of Bimetallic Sandwich in Surface-Enhanced Raman Scattering (SERS)", Colloids and Surfaces A: Physicochem. Eng. Aspects 257-258, 2005, pp. 313-317.
Zhang, H., Harnster, M.H., Park, H.J., Johnson, P.A., "Surface-Enhanced Raman Scattering Detection of DNA Derived From the West Nile Virus Genome Using Magnetic Capture of Raman-Active Gold Nanoparticles", Analytical Chemistry, Jan. 1, 2011, pp. 254-260, vol. 83(1).
Zhou, Y., Lee, C., Zhang, J., Zhang, P., "Engineering Versatile Sers-Active Nanoparticles by Embedding Reporters Between Au-Core/ Ag-Shell Through Layer-By-Layer Deposited Polyelectrolytes", J. Mater. Chem. C, 2013, pp. 3695-3699, vol. 1(23).
H. Yuan, A. M. Fales, C. G. Khoury, J. Liu, T. Vo-Dinh, "Spectral Characterization and Intracellular Detection of Surface-Enhanced Raman Scattering (SERS)-Encoded Plasmonic Gold Nanostars", J. Raman Spectroscopy, 2013, pgs. 234-239, vol. 44.
Hu, J. Zheng, P.C., Jiang, J.H., Shen, G.L., Yu, R.Q., Liu, G.K., "Sub-Attomolar HIV-1 DNA Detection Using Surface-Enhanced Raman Spectroscopy", Analyst, 2010, pp. 1084-1089, vol. 135(5).
Vo-Dinh, T., Liu, Y., Fales, A.M., Ngo, H., Wang, H.N., Register, J.K., Yuan, H., Norton, S.J., Griffin, G.D., "SERS Nanosensors and Nanoreporters: Golden Opportunities in Biomedical Applications", WIREs Nanomed Nanobiotechnology, Jan./Feb. 2015, pp. 17-33, vol. 7(1).
Darby, B.L., Etchegoin, P.G., Le Ru, E.G., "Single-Molecule Surface-Enhanced Raman Spectroscopy With Nanowatt Excitation", Phys. Chem. Chem. Phys., 2014, pp. 23895-23899, vol. 16(43).

\* cited by examiner

FIG. 1A
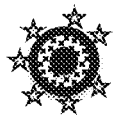
FIG. 1B
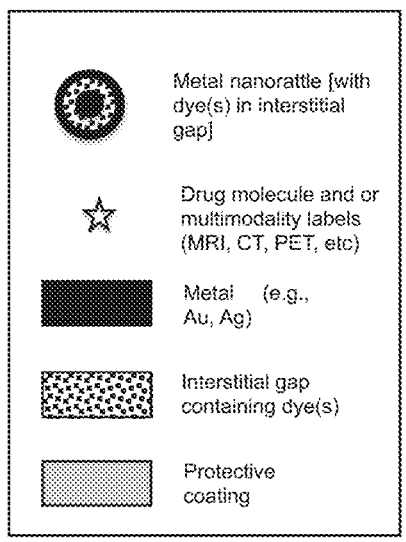
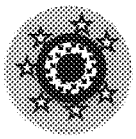
FIG. 1C
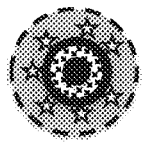
FIG. 1D
FIG. 1E
FIG. 1F
FIG. 1G
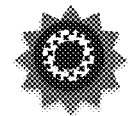
FIG. 1H

FIG. 2A
FIG. 2B
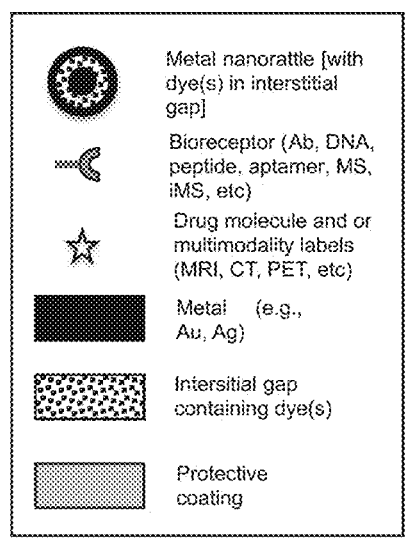
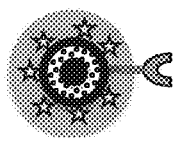
FIG. 2C
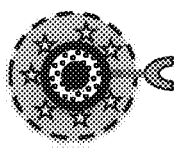
FIG. 2D
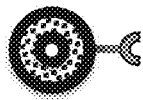
FIG. 2E
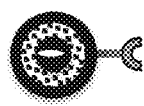
FIG. 2F
FIG. 2G
FIG. 2H $$\frac{E}{E_0} = 9\left(\frac{\varepsilon_0 \varepsilon_1 \varepsilon_3}{\varepsilon_2}\right) \frac{1}{(2\varepsilon_0 + \varepsilon_1)(2\varepsilon_1 + \varepsilon_3) + 2(\varepsilon_0 - \varepsilon_1)(\varepsilon_1 - \varepsilon_3)(R_2/R_1)^3}$$

$R_1$ = outer radius of shell $R_2$ = inner radius of shell $\varepsilon_0$ = dielectric constant of environment $\varepsilon_1$ = dielectric constant of shell $\varepsilon_2$ = dielectric constant in gap $\varepsilon_3$ = dielectric constant of core

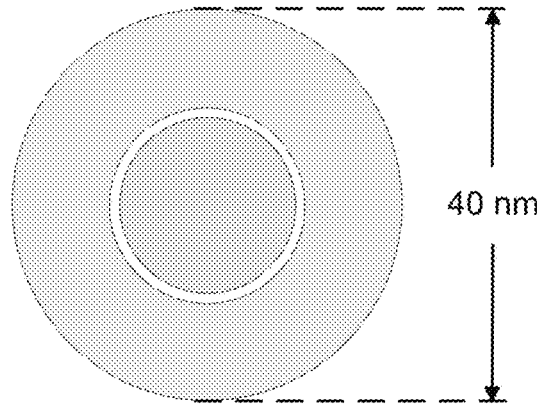

40 nm $$\varepsilon(\omega) = \varepsilon_\infty - \frac{\omega_p^2}{\omega(\omega + i\gamma)}$$

FIG. 6

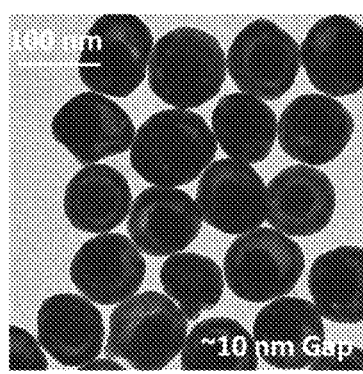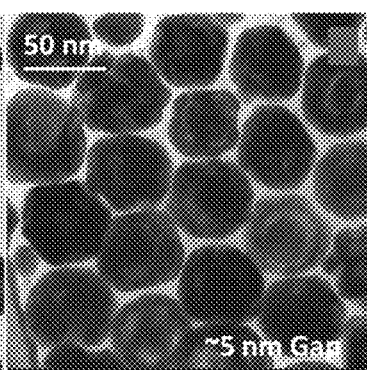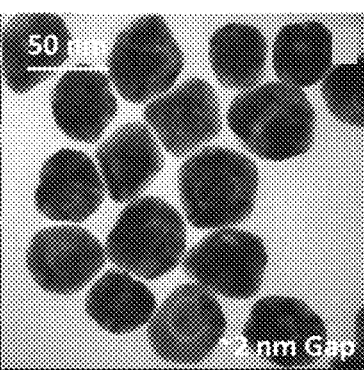
FIG. 7A  FIG. 7B  FIG. 7C
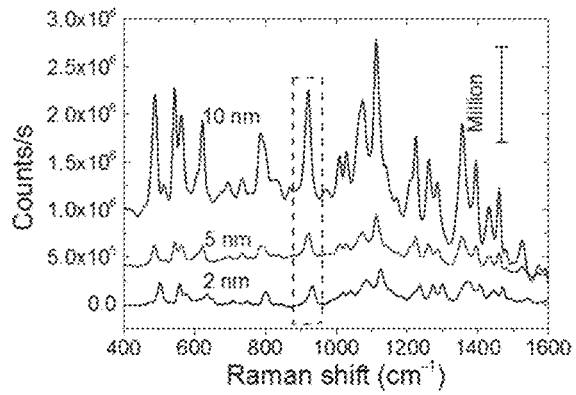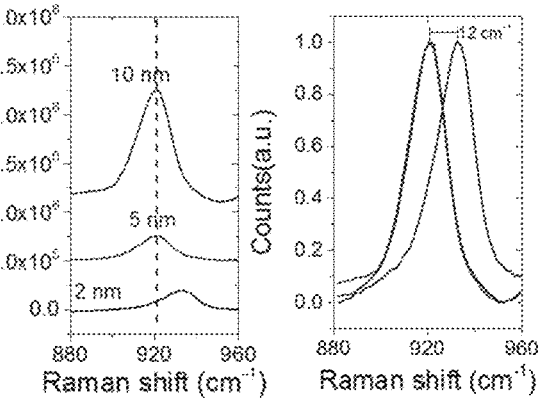
FIG. 7D  FIG. 7E  FIG. 7F

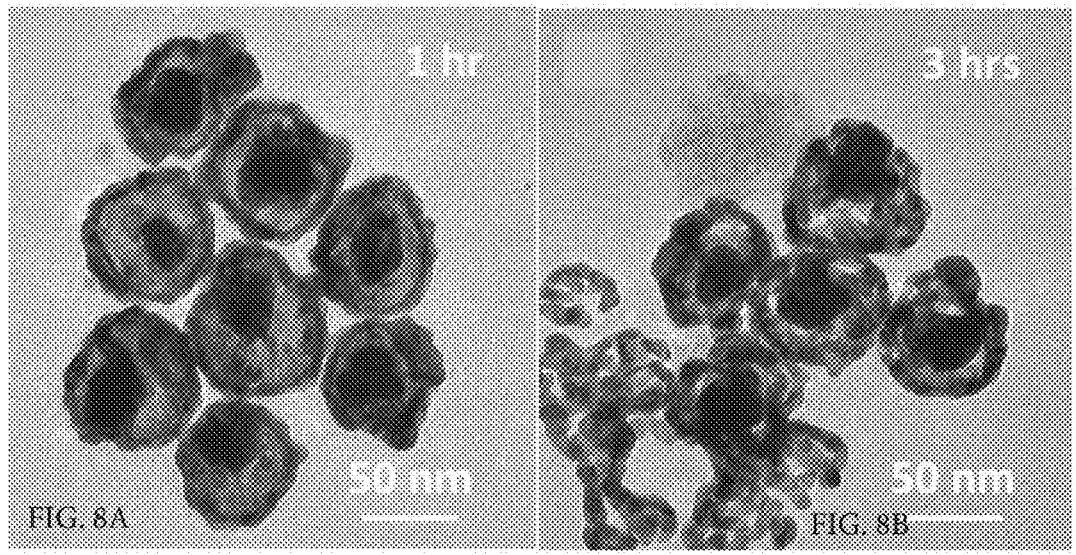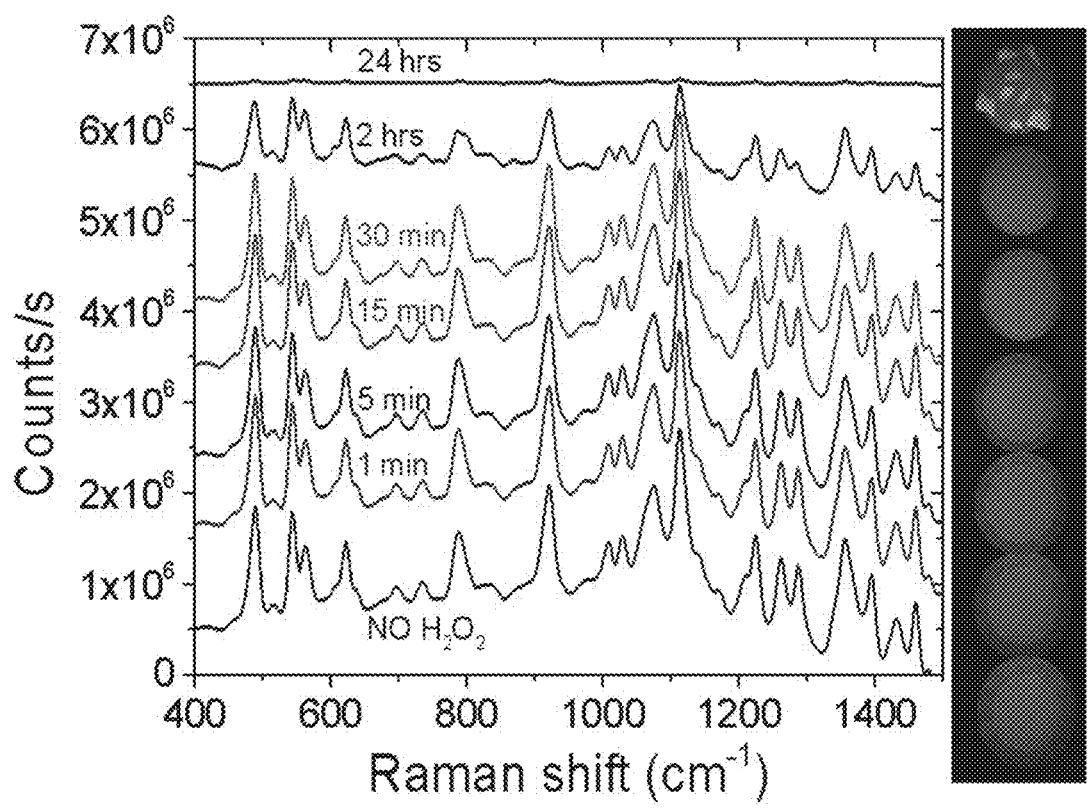
FIG. 8C

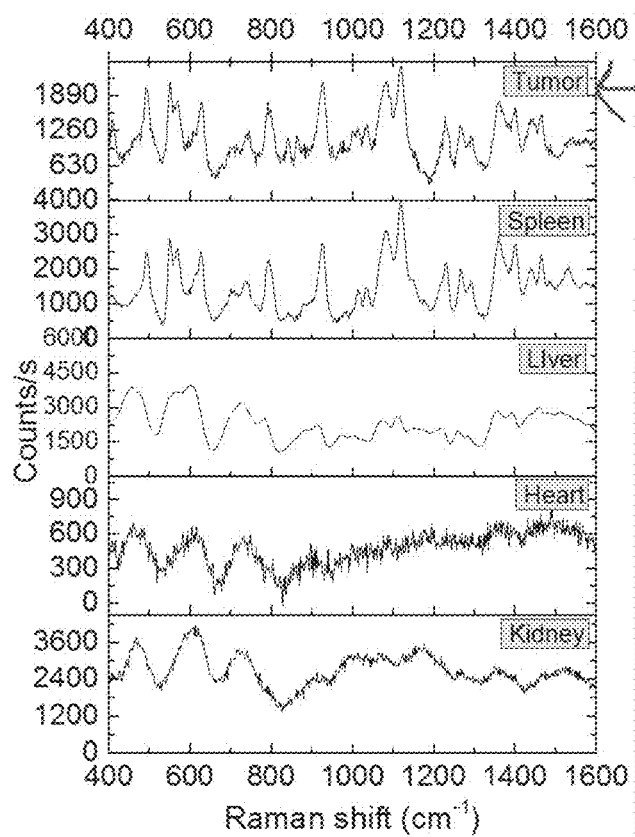
FIG. 10A
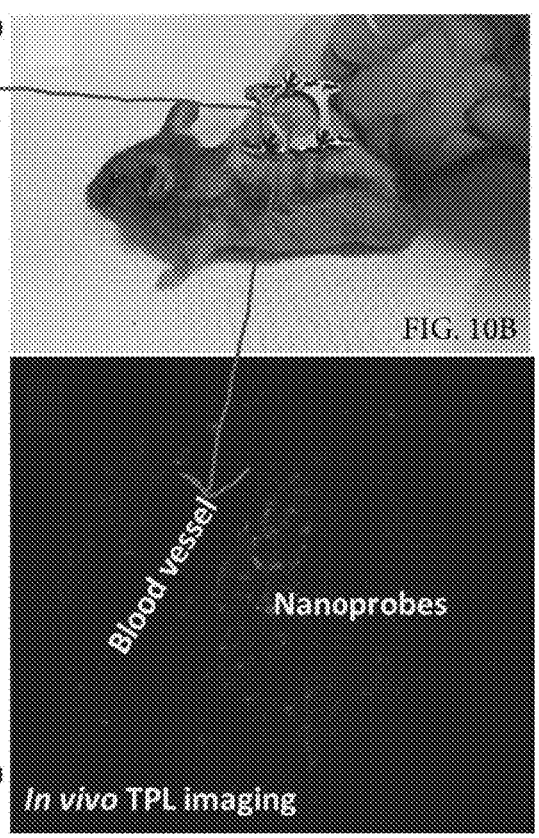
FIG. 10B
FIG. 10C

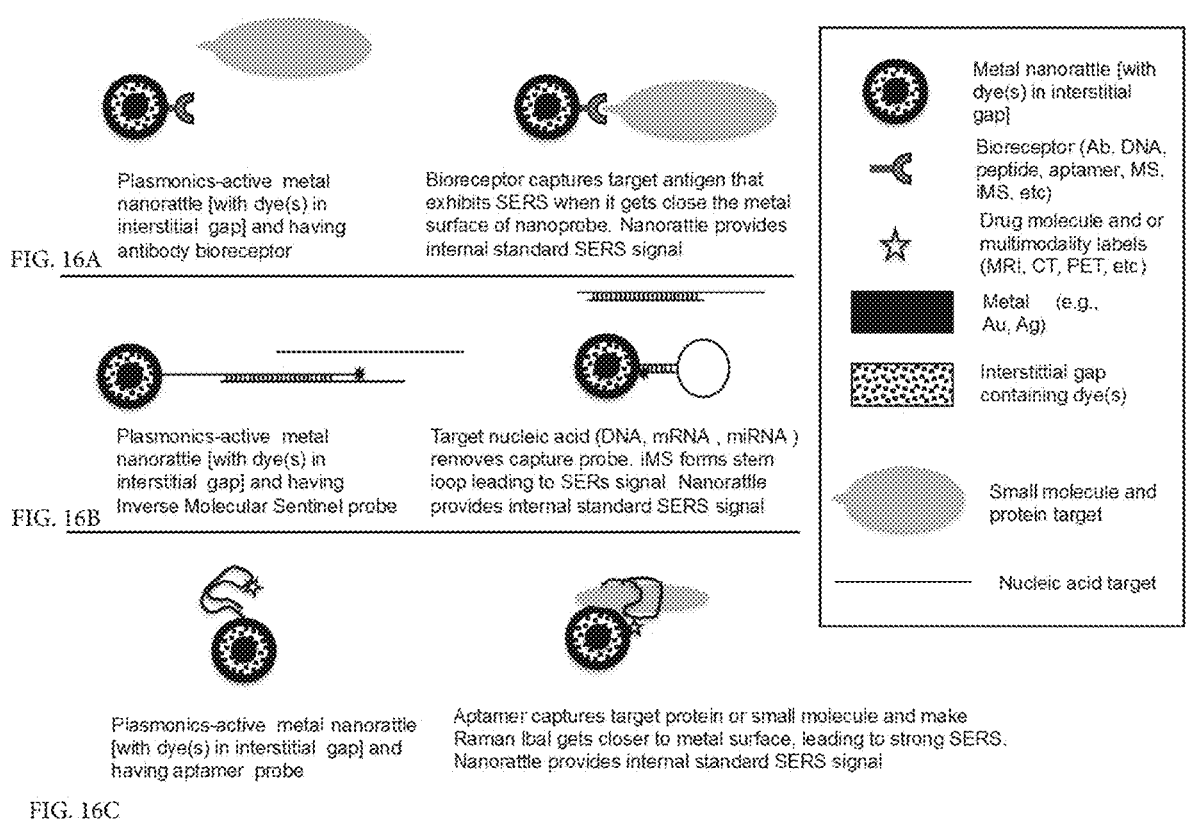

NANOPROBE COMPOSITIONS AND METHODS OF USE THEREOF

CROSS REFERENCE TO RELATED APPLICATIONS

The present application claims the benefit under 35 U.S.C. § 119(e) of U.S. Provisional Patent Application Ser. No. 62/451,106 filed on Jan. 27, 2017, the entire content of which is incorporated herein by reference.

TECHNICAL FIELD

The present disclosure relates to nanoprobe compositions and methods for use thereof for sensing and imaging in vivo and for in vitro diagnostic methods to detect DNA, RNA, proteins and other biotargets.

BACKGROUND

Surface-enhanced Raman scattering (SERS) has led to the development of SERS nanoprobes for biomedical analysis and sensing tools ranging from in vitro diagnostics to in vivo imaging. However, these nanoprobes are limited in that they are unstable in vivo due to detaching or leaking of the reporter molecules in the presence of physiological conditions often encountered in in vitro and in vivo measurements. In addition, the available nanoprobes do not allow for tunability of the type and amount of reporter molecules loaded on the nanoprobes, in order to achieve the properties required for the particular application of interest.

Several SERS nanoprobes have been developed by adsorbing and conjugating Raman reporters on metal nanostructures and doping the Raman reporter in a porous silica shell. In addition, SERS probes have been produced that that contain DNA, polymer, and 1,4-benzenedithiol (BDT) templated SERS probes in a gap between the core and the shell structures. Recent experimental and theoretical studies show that Raman reporters trapped between the core and shell of plasmonic nanostructures drastically improve the SERS signal intensity by several orders of magnitude compared to conventional nanoprobes. However, these probes remain limited to a few specific Raman dyes and the width of the gap between the core and shell is difficult to tune. Therefore, these nanoprobes fall short of achieving all the properties required for the particular application of interest.

One of the major obstacles to implement nucleic acid-based molecular diagnostics at the point-of-care (POC) and in resource-limited settings is the lack of sensitive and practical DNA detection methods that can be seamlessly integrated into portable platforms.

Molecular diagnostics is of paramount importance in medicine, biosensing, forensic science, etc. with many advantages such as high specificity, high sensitivity, serotyping capability, and mutation detection. Currently, the gold standard of nucleic acid-based molecular diagnostics tests involves polymerase chain reaction (PCR). PCR is highly sensitive with a single to few copies of target detection limit. However, it requires relatively bulky, expensive equipment, skilled workers, and is quite labor-intensive and time-consuming. Until recently, PCR tests have mainly been conducted in laboratories or hospitals. Development of rapid, easy-to-use, cost-effective, high accuracy DNA tests for molecular diagnostics at the POC and in resource-limited settings is highly needed. Such techniques will be helpful not only in developing countries but also in developed countries.

Many efforts have been devoted to develop new DNA detection methods for molecular diagnostics at the POC. Since the copy number of target DNA sequences is usually low, most of the existing methods utilize (1) target amplification or/and (2) signal amplification to achieve sufficient sensitivity. In target amplification methods (e.g. PCR, loop-mediated isothermal amplification, etc.), target sequences are amplified many million-fold using enzymatic reactions. Target amplification methods, therefore, are very sensitive. However, due to high level of amplification, trace amounts of contaminants could serve as templates and be amplified, making these methods susceptible to false positives. In addition, the presence of inhibitors can prevent enzymatic amplification, thus target purification is often required. Finally, the inherent biases in enzymatic amplifications may prevent accurate quantification.

As an alternative to target amplification, signal amplification methods can mitigate these risks, but require strong signal amplification. One method of signal amplification is SERS, a phenomenon in which Raman scattering of molecules adsorbed on metallic nanostructures is enhanced many million-fold. SERS has been reported as a sensitive analytical technique, as demonstrated by its ability to detect single molecules. Different chemical and biological sensing methods have been developed based on SERS for medical diagnostics and environmental monitoring. Compared to fluorescence, SERS has several advantages, including being more stable against photobleaching due to the extremely short lifetimes of Raman scattering. A SERS spectral peak is two orders of magnitude narrower than a fluorescence peak, making SERS more suitable for multiplex detection. With the same fluorophores, surface-enhanced resonance Raman scattering (SERRS) detection limit has been shown to be three orders of magnitude lower than of fluorescence.

SERS-based DNA detection has been investigated widely. The Mirkin group developed gold nanoparticle probes labeled with oligonucleotides and Raman-active dyes for multiplex detection of DNA with an unoptimized detection limit of 20 fM. Another group has utilized multilayer metal-molecule-metal nanojunctions to detect HIV-1 DNA at a sub-aM limit with single base mismatch discrimination. Silicon nanowires have been developed that are coated with in situ grown silver nanoparticles for DNA detection at a 1 fM limit. One group used a plasmonic nanorice and triangle nanoarray for detection of Hepatitis B virus DNA at a 50 aM limit. Although sensitive, integrating these methods into portable platforms for POC applications is still a challenge.

Malaria is a global health threat to children and adults in tropical regions. Ninety-seven countries suffer ongoing transmission of malaria parasites, which imperil 3.4 billion people annually. In 2013, malaria caused an estimated 207 million infection cases and over 600,000 deaths (WHO 2014). Mutant strains of the malaria parasite *Plasmodium falciparum* that are resistant to artemisinin drugs (Art-R), a first-line therapy for malaria, have been reported. Accordingly, it is important to develop new malaria diagnostics methods that can be used at the POC and are able to identify mutant malaria parasites.

There is an unmet need for practical, efficient, ultra bright, and stable optical labels for sensing and imaging in vivo. There is also a need for "label-free" nanoprobes for in vitro diagnostic methods to detect DNA, RNA, proteins and other biotargets. The present invention provides such improved nanoprobe compositions and methods of use thereof.

SUMMARY

In one embodiment, a method is provided for making tunable SERS nanorattles having reporter loaded in a gap between core and shell, comprising: contacting gold nanoparticle (AuNP) seeds with silver (Ag) to form an uniform width Ag shell surrounding the AuNP nanoparticle core to form a AuNP-core/Ag-shell structure (AuNP@Ag), wherein the essentially uniform width of the Ag shell is tunable; forming pores in the essentially uniform width of the Ag shell of the AuNP@Ag to form a AuNP-core/Ag-cage structure (AuNP@Cage) through galvanic replacement between Ag and $AuCl_4^-$; contacting the AuNP@Cage with a phase-change material and one or more reporter molecules to form a reporter-loaded AuNP-core/Ag-cage structure (Reporter loaded AuNP@Cage); and contacting the Reporter loaded AuNP@Cage with Au to form a Au shell encapsulating the Reporter loaded AuNP@Cage, wherein the formed structure is a nanorattle having the reporter loaded in the essentially uniform gap between core and shell (Reporter loaded SERS nanorattle). The contacting of the AuNP with Ag can include a stabilizing agent. The stabilizing agent can be polyvinylpyrrolidone (PVP). The contacting of the AuNP with Ag can include a solution of silver nitrate ($AgNO_3$). The contacting of the AuNP with Ag can further include cetyltrimethylammonium chloride (CTAC). The essentially uniform width of the Ag shell can be tunable through variation of the amount of the AuNP seeds or by variation of the amount of the $AgNO_3$. The forming of pores in the Ag shell of the AuNP@Ag can include modifying the AuNP@Ag in a solution with PVP and contacting the PVP-modified AuNP@Ag solution with a $HAuCl_4$ solution while stirring to form the AuNP@Cage. The phase-change material can comprises 1-tetradeconol. The contacting of the Reporter loaded AuNP@Cage with Au can include a solution of $HAuCl_4$ and addition of an acid. The acid can be ascorbic acid. The reporter can be a Raman dye. The reporter can be one or a combination of 2-[7-(1,3-dihydro-1,3,3-trimethyl-2H-indol-2-ylidene)-1,3,5-heptatrienyl]-1,3,3-trimethyl-3H-indolium iodide (HITC), Methylene Blue, or Rose Bengal. An average diameter of the AuNP seeds can be approximately 20 nm. An average diameter of the Reporter loaded SERS nanorattle can be approximately 50-60 nm. An average diameter of the Reporter loaded SERS nanorattle ranges from 30-110 nm. The width of the essentially uniform gap between core and shell of the Reporter loaded SERS nanorattle Reporter can be 2 nm, 5 nm, or 10 nm.

In one embodiment, a tunable SERS nanorattle is provided having reporter loaded in an essentially uniform gap between core and shell. The tunable SERS nanorattle is produced by a process comprising: contacting gold nanoparticle (AuNP) seeds with silver (Ag) to form an essentially uniform width Ag shell surrounding the AuNP nanoparticle core to form a AuNP-core/Ag-shell structure (AuNP@Ag), wherein the essentially uniform width of the Ag shell is tunable; forming pores in the essentially uniform width of the Ag shell of the AuNP@Ag to form a AuNP-core/Ag-cage structure (AuNP@Cage) through galvanic replacement between Ag and $AuCl_4^-$; contacting the AuNP@Cage with a phase-change material and one or more reporter molecules to form a reporter-loaded AuNP-core/Ag-cage structure (Reporter loaded AuNP@Cage); and contacting the Reporter loaded AuNP@Cage with Au to form a Au shell encapsulating the Reporter loaded AuNP@Cage, wherein the formed structure is a nanorattle having the reporter loaded in the essentially uniform gap between core and shell (Reporter loaded SERS nanorattle).

In one embodiment, a tunable SERS gold nanorattle is provided comprising or consisting essentially of: an essentially spherical gold metal nanoparticle core; a porous material of an essentially uniform width surrounding the nanoparticle core comprising silver metal and one or more SERS reporter molecules; and an outer gold metal shell encapsulating the porous material. The reporter can be a Raman dye. The reporter can be one or a combination of 2-[7-(1,3-dihydro-1,3,3-trimethyl-2H-indol-2-ylidene)-1,3,5-heptatrienyl]-1,3,3-trimethyl-3H-indolium iodide (HITC), Methylene Blue, or Rose Bengal. The nanorattle can have an average diameter of approximately 50-60 nm. The nanorattle can have an average diameter ranging from 30-110 nm. The essentially uniform width of the porous material can be 2 nm, 5 nm, or 10 nm. The nanorattle can comprise an attached bioreceptor selected from the group consisting of: an antibody, a nucleic acid, a peptide, an aptamer, a molecular sentinel (MS), and an inverse molecular sentinel (iMS).

In one embodiment, a method is provided of detecting a biological target molecule, the method comprising: contacting a nanorattle consisting essentially of: 1) an essentially spherical gold metal nanoparticle core, 2) a porous material of an essentially uniform width surrounding the nanoparticle core comprising silver metal and one or more SERS reporter molecules, and 3) an outer gold metal shell encapsulating the porous material, and further comprising an attached bioreceptor for the biological target molecule selected from the group consisting of: an antibody, a nucleic acid, a peptide, an aptamer, a molecular sentinel (MS), and an inverse molecular sentinel (iMS), with a sample of interest under conditions suitable for binding of the bioreceptor to the target molecule, to detect one or a combination of a presence, an absence, or a concentration of the target molecule in the sample.

In one embodiment, a kit is provided for the detection of a nucleic acid target molecule, comprising: a first nanorattle having: 1) an essentially spherical gold metal nanoparticle core, 2) a porous material of an essentially uniform width surrounding the nanoparticle core comprising silver metal and one or more SERS reporter molecules, and 3) an outer gold metal shell encapsulating the porous material, wherein the first nanorattle comprises an attached first oliognucleotide sequence complementary to a first portion of the nucleic acid target (Capture probe 1), wherein the oliognucleotide sequence comprises a first bound Raman label 1; and a second nanorattle having: 1) an essentially spherical gold metal nanoparticle core, 2) a porous material of an essentially uniform width surrounding the nanoparticle core comprising silver metal and one or more SERS reporter molecules, and 3) an outer gold metal shell encapsulating the porous material, wherein the second nanorattle comprises an attached second oliognucleotide sequence complementary to a second portion of the nucleic acid target (Capture probe 2), wherein the oliognucleotide sequence comprises a second bound Raman label 2.

In one embodiment, a kit is provided for the detection of a nucleic acid target molecule, comprising: a nanorattle having: 1) an essentially spherical gold metal nanoparticle core, 2) a porous material of an essentially uniform width surrounding the nanoparticle core comprising silver metal and one or more SERS reporter molecules, and 3) an outer gold metal shell encapsulating the porous material, wherein the nanorattle comprises an attached oliognucleotide sequence complementary to a first portion of the nucleic acid target (Reporter probe); and a magnetic bead, wherein the magnetic bead comprises an attached oliognucleotide sequence complementary to a second portion of the nucleic acid target (Capture probe).

BRIEF DESCRIPTION OF THE DRAWINGS

FIG. 1A is a schematic showing a nanorattle with dye(s) in interstitial gap. The nanorattle can provide internal standard SERS signal.

FIG. 1B is a schematic showing a nanorattle labeled with drug and dye molecules.

FIG. 1C is a schematic showing a nanorattle with drug (embedded in a protective coating).

FIG. 1D is a schematic showing a nanorattle with thermally sensitive or physiologically sensitive (e.g., pH) embedded drug.

FIG. 1E is a schematic showing a nanorattle with paramagnetic spherical innercore.

FIG. 1F is a schematic showing a nanorattle with elongated paramagnetic innercore.

FIG. 1G is a schematic showing a nanorattle with star spikes (same material).

FIG. 1H is a schematic showing a nanorattle with star spikes (different material).

FIG. 2A is a schematic showing a nanorattle with bioreceptor.

FIG. 2B is a schematic showing a nanorattle labeled with drug and bioreceptor.

FIG. 2C is a schematic showing a nanorattle with drug (embedded in a protective coating) with bioreceptor.

FIG. 2D is a schematic showing a nanorattle with drug embedded in a thermally sensitive or physiologically sensitive (e.g., pH) with bioreceptor.

FIG. 2E is a schematic showing a nanorattle with paramagnetic spherical inner core with bioreceptor.

FIG. 2F is a schematic showing a nanorattle with elongated paramagnetic inner core with bioreceptor.

FIG. 2G is a schematic showing a nanorattle with star spikes (same material) with bioreceptor.

FIG. 2H is a schematic showing a nanorattle with star spikes (different material) with bioreceptor.

FIG. 6 shows the equations for calculating the electric field enhancement ($E/E_o$) and for tuning the plasmon band of the gold nanorattles: Finite element method (FEM) calculations of TARGETs with varying shell thickness, core size, and gap size (COMSOL Multiphysics v4.3 software). The E-field distribution inside the gap significantly changes with shell, core, and gap dimensions of the nanorattle.

FIG. 7A illustrates tuning the gap between core and shell versus SERS and is a TEM image of HITC molecules trapped in a nanorattle with a 10 nm gap between core and shell.

FIG. 7B illustrates tuning the gap between core and shell versus SERS and is a TEM image of HITC molecules trapped in a nanorattle with a 5 nm gap between core and shell.

FIG. 7C illustrates tuning the gap between core and shell versus SERS and is a TEM image of HITC molecules trapped in a nanorattle with a 2 nm gap between core and shell.

FIG. 7D illustrates tuning the gap between core and shell versus SERS and is a SERS spectrum of nanorattles having 10 nm, 5 nm, and 2 nm gaps.

FIG. 7E illustrates tuning the gap between core and shell versus SERS and is a graph showing the Raman shift of corresponding nanorattles with 10 nm, 5 nm, and 2 nm gaps.

FIG. 7F illustrates tuning the gap between core and shell versus SERS and is a graph showing significant upshift (12 $cm^{-1}$) in the case of the nanorattle having a 2 nm gap.

FIG. 8A illustrates tuning the gap between core and shell versus SERS and shows SERS of HITC present between core and shell of nanorattles with a 10 nm gap and a 10 nm thick shell in 3% $H_2O_2$ over time and is a TEM image showing nanorattles with a 10 nm gap and a 10 nm thick shell after 1 hour in 3% $H_2O_2$.

FIG. 8B illustrates tuning the gap between core and shell versus SERS and shows SERS of HITC present between core and shell of nanorattles with a 10 nm gap and a 10 nm thick shell in 3% $H_2O_2$ over time and is a TEM image showing nanorattles with a 10 nm gap and a 10 nm thick shell after 3 hours in 3% $H_2O_2$.

FIG. 8C illustrates tuning the gap between core and shell versus SERS and shows SERS of HITC present between core and shell of nanorattles with a 10 nm gap and a 10 nm thick shell in 3% $H_2O_2$ over time and is a graph showing there is no significant difference in SERS with and without $H_2O_2$ in first the 30 min (as indicated by comparing No $H_2O_2$, 1 min, 5 min, 15 min, 30 min). However, after 24 hrs the intensity of the SERS significantly decreased mainly due to the formation of pores, complete etching of shell, and degradation of HITC in peroxide solution.

FIG. 10A shows use of the nanorattles for in vivo sensing and imaging and shows SERS signals of intravenously injected nanoprobes in immune competent mouse after 24 hrs. Strong SERS signals were detected in both tumor and spleen, which indicated our SERS probes were not affected by the immune competent mouse.

FIG. 10B shows use of the nanorattles for in vivo sensing and imaging and shows an immune responsive mouse with Lewis Lung Carcinoma (LLC) tumor in a dorsal window chamber.

FIG. 10C shows use of the nanorattles for in vivo sensing and imaging and shows in vivo two photon luminescence of TARGETs obtained from the tumor location after 24 hrs of circulation, which indicates that TARGETs accumulated in the tumor due to its leaky vasculature

FIG. 16A is a schematic diagram showing multiple probe designs using a nanorattle and various bioreceptors where the dye inside the nanorattle can be used as an internal standard and shows a nanorattle having an antibody receptor.

FIG. 16B is a schematic diagram showing multiple probe designs using a nanorattle and various bioreceptors where the dye inside the nanorattle can be used as an internal standard and shows a nanorattle having an inverse Molecular Sentinel (iMS) probe.

FIG. 16C is a schematic diagram showing multiple probe designs using a nanorattle and various bioreceptors where the dye inside the nanorattle can be used as an internal standard and shows a nanorattle having an aptamer probe.

DETAILED DESCRIPTION

Figure 3:
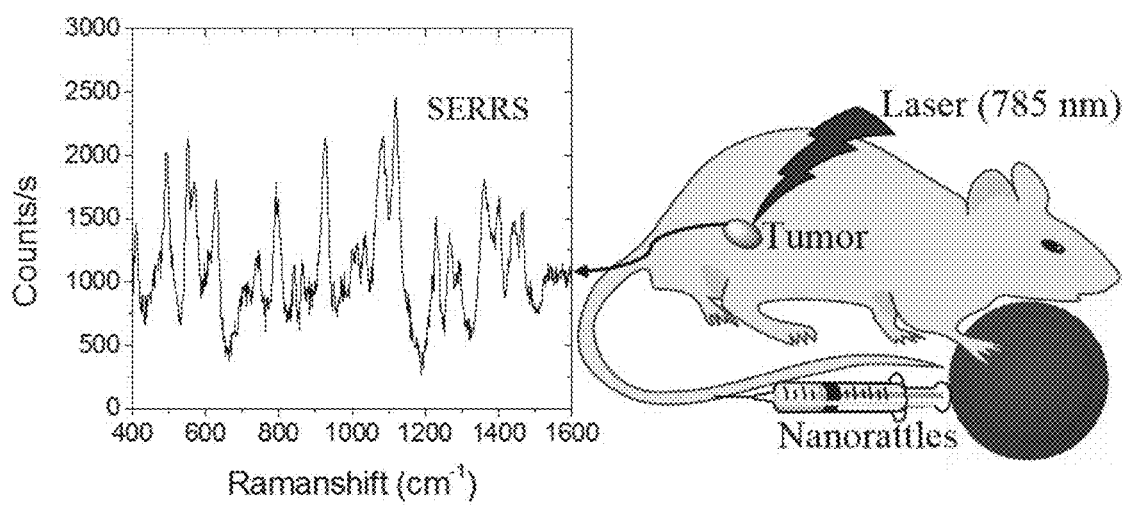
FIG. 3 is a schematic showing the usefulness of the nanorattles for in vivo applications.

For the purposes of promoting an understanding of the principles of the present disclosure, reference will now be made to preferred embodiments and specific language will be used to describe the same. It will nevertheless be understood that no limitation of the scope of the disclosure is thereby intended, such alteration and further modifications of the disclosure as illustrated herein, being contemplated as would normally occur to one skilled in the art to which the disclosure relates.

Articles "a" and "an" are used herein to refer to one or to more than one (i.e. at least one) of the grammatical object of the article. By way of example, "an element" means at least one element and can include more than one element.

As used herein, the term "about" or the term "approximately", when referring to a value or to an amount of distance, diameter, mass, time, volume, concentration, and/or percentage can encompass variations of, in some embodiments +/−20%, in some embodiments +/−10%, in some embodiments +/−5%, in some embodiments +/−1%, in some embodiments +/−0.5%, and in some embodiments +/−0.1%, from the specified amount, as such variations are appropriate in the disclosed compositions and methods. Alternatively, particularly with respect to biological systems or processes, the term can mean within an order of magnitude, preferably within 5-fold, and more preferably within 2-fold, of a value. Where particular values are described in the application and claims, unless otherwise stated the term "about" meaning within an acceptable error range for the particular value should be assumed.

Unless otherwise defined, all technical terms used herein have the same meaning as commonly understood by one of ordinary skill in the art to which this disclosure belongs.

In one embodiment surface-enhanced Raman scattering (SERS) nanoprobes are provided having a tunable gap between the core and shell. This core-shell nanostructure is comprised of one or more resonance Raman reporters trapped between the core and shell, which acts as an ultra bright SERS probe as a result of a strong and localized electric field due to plasmonic coupling at core-shell junctions. For the purposes of the specification and claims, the "nanostructures" or "nanoparticles" of the present disclosure having one or more resonance Raman reporters trapped between the core and shell are also referred to interchangably as "nanorattles", "nanoprobes", "SERS nanoprobes", or "SERS nanostructures." The SERS nanostructures of the present disclosure are highly tunable, physiologically stable, and ultra-bright Raman probes, for in vitro and in vivo SERS applications. Also for the purposes of the specification and claims, the terms "dye", "reporter", "reporter molecule", "Raman reporter", and "label" are herein used interchangeably.

In one embodiment, gold nanorattle probes are provided that are highly tunable, physiologically stable, and ultra-bright Raman probes for in vitro and in vivo surface-enhanced Raman scattering (SERS) applications. The nanorattles contain an essentially uniform gap beteween core and shell that is tunable and can range from 2 nm to 10 nm in width. This provides numerous advantages including allowing for increased loading with a variety of dye molecules that exhibit SERS in various spectral regions, including the "tissue optical window" for in vivo studies. In addition, the nanorattle probes provide an internal label when used in diagnostic methods to detect nucleic acids, proteins and other biotargets. The nanorattles have an essentially spherical gold metal nanoparticle core, a porous material of silver metal of an essentially uniform width surrounding the nanoparticle core that is loaded with one or more SERS reporter molecules, and an outer gold metal shell encapsulating the porous material.

Unlike previously developed "bilayered Raman intense gold nanostrcutures with hidden tags" (BRIGHTs) in which 1,4- benzenethiol (BDT) is required to form a gap between the core and shell, the nanoprobes of the present disclosure have a tunable core-shell gap of an essentially uniform width that allows for loading of any chosen resonance or nonresonance Raman reporter. Another advantage of the presently disclosed core-shell nanostructures is a tunable core-shell gap that allows for loading of multiple Raman reporters, which can be used for multiplexing.

The nanorattles of the present disclosure can have a wide range of structures as shown in FIG. 1. Specifically, FIG. 1 shows the various embodiments of the probes based on nanorattles: (A) Plasmonics-active metal nanorattle [with dye(s) in interstitial gap]. The nanorattle can provide internal standard SERS signal; (B) Nanorattle labeled with drug and dye molecules; (C) Nanorattle with drug (embedded in a protective coating); (D) Nanorattle with thermally sensitive or physiologically sensitive (e.g., pH) embedded drug; (E) Nanorattle with paramagnetic spherical innercore; (F) Nanorattle with elongated paramagnetic innercore; (G) Nanorattle with star spikes (same material); and (H) Nanorattle with star spikes (different material).

Physiological stability of SERS probes is an important feature for biomedical applications. In the nanorattles disclosed herein, the well-protected reporter molecules inside the core-shell gap are not accessible to physiological fluids and as a result can provide consistent SERS signals. Thus, in one embodiment, the SERS-nanostructures are suitable for use as internal reference standards.

Bioreceptors can be used to target the nanoprobes of the present disclosure such as, for example, to target the nanoprobes to disease cells, tumors, mutant genes, specific genes, or protein markers. These bioreceptors can take many forms and the different bioreceptors that have been used are as numerous as the different analytes that have been monitored using biosensors. FIG. 2 is a schematic showing examples of various nanorattle probes of the present disclosure labeled with bioreceptors. The nanorattle probes are similar to those shown in FIG. 1, but also include a bioreceptor for targeting. The bioreceptors include, but are not limited to: 1) antibody/antigen, 2) enzymes, 3) nucleic acids/DNA, 4) cellular structures/cells and 5) biomimetic (aptamers, peptides, etc). Specifically, FIG. 2 shows: (A) Nanorattle with bioreceptor; (B) Nanorattle labeled with drug and bioreceptor; (C) Nanorattle with drug (embedded in a protective coating) with bioreceptor; (D)Nanorattle with drug embedded in a thermally sensitive or physiologically sensitive (e.g., pH) with bioreceptor; (E) Nanorattle with paramagnetic spherical inner core with bioreceptor; (F) Nanorattle with elongated paramagnetic inner core with bioreceptor; (G) Nanorattle with star spikes (same material) with bioreceptor; (H) Nanorattle with star spikes (different material) with bioreceptor.

Methods for labeling gold/silver nanostructures with bioreceptors are known in the art. The majority of immobilization schemes involving Au(Ag) surfaces utilize a prior derivatization of the surface with alkylthiols, forming stable linkages. Alkylthiols readily form self-assembled monolayers (SAM) onto silver surfaces in micromolar concentrations. The terminus of the alkylthiol chain can be used to bind bioreceptors, or can be easily modified to do so. The majority of synthetic techniques for the covalent immobilization of biomolecules utilize free amine groups of a polypeptide (enzymes, antibodies, antigens, etc) or of amino-labeled DNA strands, to react with a carboxylic acid moiety forming amide bonds. As a general rule, a more active intermediate (labile ester) is first formed with the carboxylic acid moiety and in a later stage reacted with the free amine, increasing the coupling yield. Successful coupling procedures include the use of N-hydroxysuccinimide (NHS) and its derivatives, Maleimide, and Carbodiimide according to procedures well know in the art.

Nanorattle probes are provided that are highly tunable, physiologically stable, and ultra-bright Raman probes for in vitro and in vivo surface-enhanced Raman scattering (SERS) applications. An improved property of the nanorattle structures of the present disclosure is that they allow for inclusion of various dye molecules that exhibit SERS in various spectral regions as compared to the prior structures. The nanorattle structure consists of a gold core inside a larger gold shell with a tunable and uniform interstitial gap. The combination of galvanic replacement and the seed mediated growth method was employed to load Raman reporter molecules and to subsequently close the pores to prevent leaking and degradation of reporters under physiologically extreme conditions. Precise tuning of the core-shell gap width, core size, and shell thickness allows for modulation of the plasmonic effect and achievement of a maximum electric-field (E-field) intensity. The interstitial gap of the nanorattles can be designed to exhibit a plasmon absorption band at 785 nm, which is in resonance with the dye absorption maximum and lies in the "tissue optical window", resulting in ultra-bright SERS signals for in vivo studies. A schematic exemplifying the in vivo use of the nanorattle probes is shown in FIG. 3.

The tunability of the SERS signal of the nanorattles of the present invention is multifactoral and governed by the spectral absorption properties of the reporter, excitation wavelength, extinction of the probe, gap size, and loading capacity of reporter molecules between the core and shell. Indeed, the optical properties of the nanorattles can be highly customized to specific excitation wavelengths by carefully tuning the gap width and choosing the resonance reporter specific to the wavelengths of interest. The advantages of nanorattles compared to other SERS probes are: (i) a highly tunable gap with a well defined core-shell thickness and interstitial gap desired for wavelength specific E-field enhancement, (ii) an ultrabright SERS signal due to strong plasmonic coupling, (iii) physiologically stable reporters protected inside the gap, (iv) consistant and fluorescence free SERS signal from the resonance Raman reporter molecules present in interstitial gap, and (v) potential for multiplex sensing.

Figures 4A, 4B:
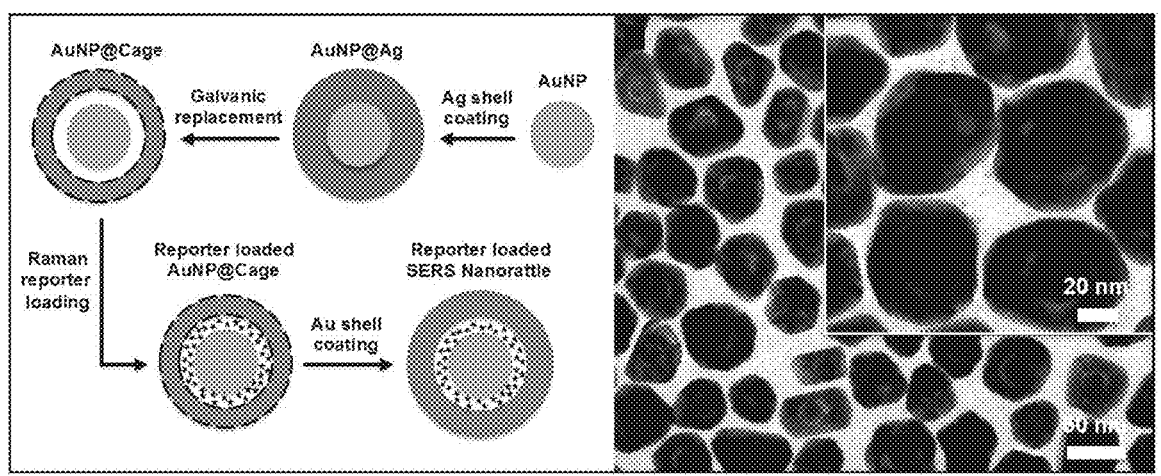
FIG. 4A is a schematic diagram showing the SERS nanorattle synthesis process.
FIG. 4B is a TEM image of nanorattles with a core-gap-shell structure (inset: higher magnification TEM image). Raman reporters were loaded into the gap space between the core and the shell.

FIGS. 4 and 5 illustrate the process of preparing nanorattles of the present invention. First, gold nanoparticles (AuNP) are contacted with silver (Ag) to form a silver shell surrounding the AuNP core to form a AuNP-core/Ag-shell structure (AuNP@Ag). In one embodiment, 20-nm AuNPs are used as seed templates to grow a 15-nm thick silver shell. Next, the silver shell is used as a sacrificial template to synthesize porous "gold/silver nanocages". Specifically, pores are formed in the silver shell of the AuNP-core/Ag-shell structure to form a porous AuNP-core/Ag-cage structure. Galvanic replacement can be used to form the pores in the Ag shells to create the porous AuNP-core/Ag-cage structure containing the AuNP core (AuNP@Cage) according to methods known to those of ordinary skill in the art. As a result of the production of pores, Raman reporters are then loaded into the AuNP-core/Ag nanocage (AuNP@Cage) with the assistance of a phase-change material such as, for example, 1-tetradecanol, according to methods known to those of ordinary skill in the art. The porous cages are then converted to complete shells by a final gold coating to form the SERS nanorattles. The gold coating can be 5-15 nM in thickness. The gold shell grown on the top of the AuNP-core/Ag nanocage closes the pores and prevents the Raman reporter molecules from leaking out even in physiologically stringent conditions. TEM images of the synthesized SERS nanorattles are shown in FIG. 4B and FIG. 5B-D. The average particle size of the nanorattles shown is approximately 60 nm. The core-gap-shell structure is observable in the nanorattles and has a well-defined gap. In addition, different thicknesses of sacrificial silver templates can be used including 5, 10 and 20 nm to produce a variation in the gap between the core and the shell of the nanorattles. UV-vis extinction spectra can depict the differences in size and gap of the nanorattles. SERS-encoded nanorattles of the present invention have Raman reporters in the gap space between the core and the shell. The Raman reporters can be HITC Raman reporters. In contrast to prior art Au/Ag nanocages that can degrade in vivo, the presently described approach not only stops the leaking of the reporter dye molecules but also makes them highly stable under in vivo conditions.

In one embodiment, a method is provided for making tunable SERS nanorattles having reporter loaded in a gap between core and shell, comprising: contacting gold nanoparticle (AuNP) seeds with silver (Ag) to form an uniform width Ag shell surrounding the AuNP nanoparticle core to form a AuNP-core/Ag-shell structure (AuNP@Ag), wherein the essentially uniform width of the Ag shell is tunable; forming pores in the essentially uniform width of the Ag shell of the AuNP@Ag to form a AuNP-core/Ag-cage structure (AuNP@Cage) through galvanic replacement between Ag and $AuCl_4^-$; contacting the AuNP@Cage with a phase-change material and one or more reporter molecules to form a reporter-loaded AuNP-core/Ag-cage structure (Reporter loaded AuNP@Cage); and contacting the Reporter loaded AuNP@Cage with Au to form a Au shell encapsulating the Reporter loaded AuNP@Cage, wherein the formed structure is a nanorattle having the reporter loaded in the essentially uniform gap between core and shell (Reporter loaded SERS nanorattle).

In one embodiment, a tunable SERS nanorattle is provided having reporter loaded in an essentially uniform gap between core and shell. The tunable SERS nanorattle is produced by a process comprising: contacting gold nanoparticle (AuNP) seeds with silver (Ag) to form an essentially uniform width Ag shell surrounding the AuNP nanoparticle core to form a AuNP-core/Ag-shell structure (AuNP@Ag), wherein the essentially uniform width of the Ag shell is tunable; forming pores in the essentially uniform width of the Ag shell of the AuNP@Ag to form a AuNP-core/Ag-cage structure (AuNP@Cage) through galvanic replacement between Ag and $AuCl_4^-$; contacting the AuNP@Cage with a phase-change material and one or more reporter molecules to form a reporter-loaded AuNP-core/Ag-cage structure (Reporter loaded AuNP@Cage); and contacting the Reporter loaded AuNP@Cage with Au to form a Au shell encapsulating the Reporter loaded AuNP@Cage, wherein the formed structure is a nanorattle having the reporter loaded in the essentially uniform gap between core and shell (Reporter loaded SERS nanorattle).

In one embodiment, a tunable SERS gold nanorattle is provided comprising or consisting essentially of: an essentially spherical gold metal nanoparticle core; a porous material of an essentially uniform width surrounding the nanoparticle core comprising silver metal and one or more SERS reporter molecules; and an outer gold metal shell encapsulating the porous material.

Figure 5A:
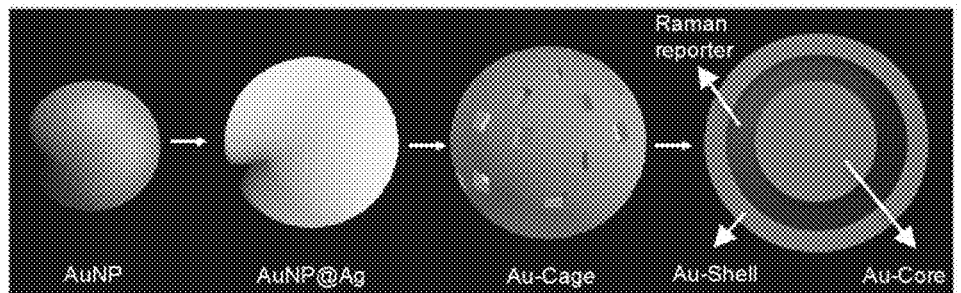
FIG. 5A shows the design, synthesis, and loading of reporters between gold core and gold outer shell with a schematic representation of the design and synthesis of core-shell SERS probe with a gap.
Figures 5B, 5C, 5D:
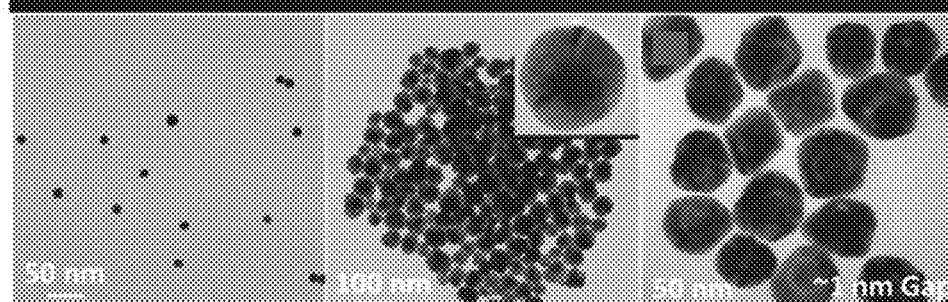
FIG. 5B is a TEM image of gold core nanoparticles (AuNP) synthesized in Turkevich method.
FIG. 5C is a TEM image of Ag@AuNP nanostructures with ~20 nm thick silver shell on shell.
FIG. 5D is a TEM image of nanorattles with a 1 nm gap between the core and shell.
Figure 5E:
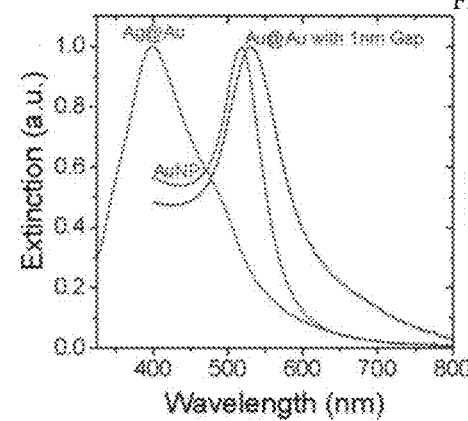
FIG. 5E is a UV-vis extinction spectra of AuNP, Ag@AuNP, and gold core-shell, which are mentioned above depicting the optical properties of the structures.
Figure 5F:
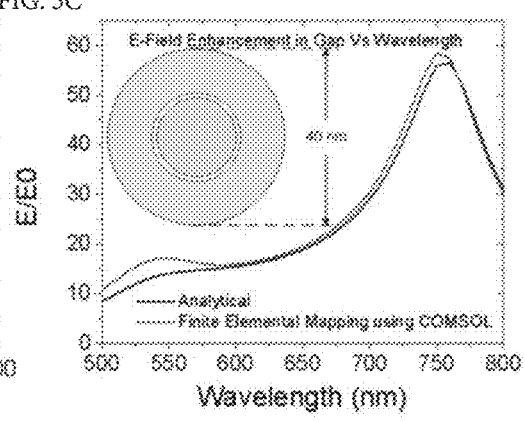
FIG. 5F is a COMSOL model and analytical calculation of the E-field enhancement in the gap at different excitation wavelengths, which predicts 40 nm nanorattle with a 1 nm gap has highest E-field at 750 nm. Both analytical and finite elemental mappings are in good agreement with each other.

UV/Vis absorption spectra indicate the change in optical properties when the AuNP (plasmon absorption at 518 nm) transforms to silver-coated AuNP "AuNP@Ag" (plasmon absorption at 400 nm) followed by galvanic replacement and shell growth to form reporter loaded SERS nanorattles (plasmon absorption at 530 to 550 nm) FIG. 5E. Depending on the gap and size of the nanorattle, the extinction maximum can vary between 525 nm and 550 nm with a shoulder between 600 and 700 nm. The intensity and position of the shoulder depends on the size of the gap between the core and shell (FIG. 5E). This shoulder is more obvious if the gap between the core and shell is larger than 5 nm. COMSOL calculations show the maximum E-field is concentrated between the core and shell at 755 nm with a 40 nm diameter nanorattle, 1 nm gap between the core and shell, and 10 nm shell thickness (40 nm(10-1-18)). Simulations are in good agreement with analytical calculations as is shown in FIG. 5F.

SERS measurements showed that SERS nanorattles exhibit intense SERS signal, more than three orders of magnitude stronger than gold nanospheres coated with the same Raman reporters. The nanorattle's intense SERS brightness was attributed to two factors. First, with a nano-size gap space between the nanorattle's core and shell, the nanorattle can be loaded with a higher number of Raman reporters in comparison with number of reporters in a monolayer coating on a gold nanosphere's surface. Second, the E field enhancement in the gap space of the nanorattle was estimated to be several times higher than the enhancement on gold nanosphere's surface. Since SERS enhancement strongly depends on E field enhancement with a fourth power dependence, such increases in E field enhancement of nanorattles would result in several orders of magnitude increase in SERS enhancement.

To calculate the increase in E field enhancement of the nanorattle, a 3-D model of the nanorattle was built. Simulations show that the Raman reporters between the core and shell exhibit a maximum E-field between 600 and 900 nm depending on the shell thickness, core size, and gap size (FIG. 6), which is important for both in vitro and in vivo SERS applications. The model was excited by an incident plane wave, and total electromagnetic field was solved. Ratio of total E field and incident E field, denoted $|E|/|E_{in}|$— the E field enhancement, was calculated and plotted. Calculation results show the strong E field enhancement in the gap space of the nanorattle with the highest enhancement of about 14.10 times. This result is in agreement with previous results on a similar structure, the silica-insulated concentric structure. Compared to the highest E field enhancement of a gold nanosphere with similar size, which was about 3.44 times, the nanorattle's was 4.1 times higher. Similar improvements in E field enhancement were also observed when comparing the nanorattle with the nanorattle's shell alone or with the nanorattle's core alone. The highest E field enhancement of the nanorattle's shell alone was 3.53 times while that of the nanorattle's core alone was 3.33 times. However, when both the core and the shell were combined into a nanorattle with core-gap-shell structure, the highest E field enhancement was 14.10 times as mentioned above.

The strong E field enhancement in the gap space of the nanorattle can be explained by the coupling of surface plasmons of the metal core and the metal shell. This strong E field enhancement between the core and the shell has been harnessed by several previous works for SERS enhancement. Also in the previous described work, only a monolayer of Raman reporters was loaded into the gap space by using self-assembly of reporters on a core followed by a shell coating. In contrast, the nanorattles of the present invention have greater Raman reporter loading capacity, because the core-gap-shell structures are first synthesized, and then the Raman reporters are loaded into the gap space. Since the gap is nanometer in scale, the nanorattle of the present invention has higher reporter loading capacity.

The SERS characteristics of the reporter molecules trapped between the core and shell of the nanorattles were studied. Specifically, the SERS signal of 2-[7-(1,3-dihydro-1,3,3-trimethyl-2H-indol-2-ylidene)-1,3,5-heptatrienyl]-1,3,3-trimethyl-3H-indolium iodide (HITC) molecules trapped in three different nanorattles with 2, 5, and 10 nm gaps were analyzed (FIG. 7A-7F). The SERS intensity of HITC from the nanorattles having a 10-nm gap was 4.0±0.5 times higher than those with 5-nm and 2-nm gaps. Without being limited to any particular mechanism of action, this could be explained by the presence of a larger numbers of HITC molecules in the 10 nm gap. However, no significant difference was observed in SERS enhancement between nanorattles having 2 and 5 nm gaps, which again without being limited to a particular mechanism of action, could be due to the trade-off between the E-field enhancement and loading capability. The SERS signal shows a 12 cm$^{-1}$ upshift in peak position in the case of the 2-nm gap nanorattles compared to the 5-nm and 10-nm gap nanorattles. Without being limited to any particular mechanism of action, the upshift in Raman frequency of HITC in the 2-nm gap could be due to the molecular compression of the dye molecules inside the narrow gaps, which is consistent with previous reports where BDT molecules show significant upshift in peak position when they are bridged between the two gold layers with a 0.65-nm gap. One significant advantage of the nanorattles of the present disclosure is a lack of fluorescence background from the HITC molecules present in the interstitial gap, which obviates the need to subtract background signal from the SERS signal.

The gold nanorattles (loaded with Raman reporters) of the present invention exhibit ultrabright SERS signal that can be more than 1000-fold stronger than gold_nanospheres of the prior art that are coated with the same Raman reporters.

Studies were performed to confirm that the strong Raman enhancement observed for the nanorattles resulted from the dye molecules present between the core and shell of the nanorattle structure, and not from the dye molecules adsorbed onto the nanorattle outer surfaces. Specifically, etching studies using $H_2O_2$ were performed in order to study the effect of SERS intensity over time (FIGS. 8A-8C). If the HITC dye molecules are adsorbed only on the outer surface, the SERS signal is expected to completely diminish in minutes after $H_2O_2$ etching since the cyanine dyes are known to degrade in peroxide solutions. However, the SERS intensity was stable up to 2 hrs after the $H_2O_2$ addition, which confirms that HITC molecules are not on the surface (FIG. 8C). After 6 hrs the SERS signal was drastically reduced, mainly due to the rupture of the shell, which triggered leaking and degradation of reporter molecules. This TEM analysis also confirmed the etching and rupture of the shell at 1 and 3 hrs after $H_2O_2$ addition (FIGS. 8A-8B).

In addition to the nanorattles described above loaded with HITC molecules, additional nanorattles were synthesized and loaded with two additional Raman reporters, Rose Bengal and Methylene Blue for comparative SERS measurements with HITC at 785 nm. After loading these three dyes in three different nanorattles having 10-nm gaps, maximum SERS intensity was achieved in the case of HITC followed by Methylene Blue, but only a weak SERS signal was observed for Rose Bengal. In order to achieve maximum SERS there must be an overlap between the absorption of the resonance reporter, the E-field peak spectrum inside the gap, and the excitation wavelength of the laser.

Figure 9:
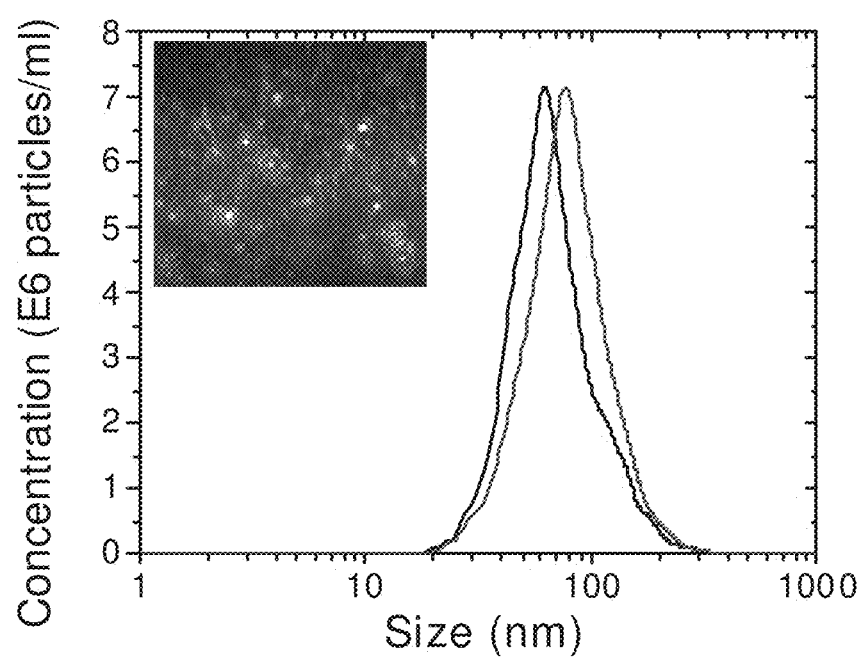
FIG. 9 is a graph illustrated the size and concentration of the nanorattles of the present invention diluted 1000 fold from the original concentration after synthesis.

In one embodiment, FIG. 9 illustrates the size and concentration of the nanorattles of the present invention diluted 1000 fold from the original concentration after synthesis.

Besides exhibiting intense SERS brightness, the core-gap-shell structure with Raman reporters trapped in the gap space between the core and the shell has several additional advantages. First, since the reporters are protected by a metal shell, chemical stability is improved with regard to signal degradation, as reporter desorption can be prevented. Reporter protection using silica shells has been reported previously. Second, since the reporters are trapped inside the nanorattle structure instead of coated on the structure's outer surface, the whole outer surface of the nanorattle is available for DNA probe functionalization (or other bioreceptor functionalization). This allows more flexibility in tuning DNA probe/bioreceptor density for optimal hybridization/target binding efficiency without compromising the SERS brightness. Third, in contrast to SERS enhancement based on nanojunctions between aggregated nanoparticles (a.k.a. SERS "hot spots") that are difficult to control and have poor reproducibility, the SERS enhancement of the nanorattles of the present invention is based on the nano-sized gap between the core and shell, which is easier to control and more reproducible.

In one embodiment, to assess the physiological stability, rattles were incubated with breast epithelial cell in culture and the SERS signal collected at different time points. The color of the cells after 5 hrs of incubation with the nanorattles was dark as compared to control cells and medium alone (data not shown), which indicated the nanorattles were passively internalized and/or adsorbed on cellular membranes. The intensity of the SERS signal was stable even after 24 hrs of incubation, which indicated no degradation of either the nanorattles or the reporter molecules in the cellular system. SERS mapping was performed to confirm the distribution of the nanorattles in single cells. The SERS mapping results using a 630-nm (10 mW) laser with 1-micron spatial resolution indicated the nanorattles were distributed evenly in the cellular system. The SERS imaging data confirmed the stability of the reporter molecules inside the nanorattles even after extensive exposure to cellular enzymes.

In another embodiment, the stability of the nanorattle nanoprobes was determined in live animals and tumoregenic conditions. Specifically, nanorattles were directly injected into the Lewis Lung carcinoma tumor in an athymic immune compromised mouse (commonly known as nude mouse) with a dorsal window chamber and the SERS signal monitored over time (FIG. 10). SERS signal from the nanorattles was collected for 1 s using a fiber optic probe and a 785-nm laser (100 mW) after 15 min, 30 min, 5 hrs, and 24 hrs post-injection. Even 24 hrs after injection of the nanorattles, the SERS signal was detectable and a decrease in signal intensity was observed between 5 hrs and 24 hrs. Without being limited to any particular mechanism of action, it is believed that the drop in SERS intensity was due to the fact that some of the nanorattles entered into the blood circulation. The experimental results from SERS signals collected from various tissues in the animal showed that the nanorattles are highly stable to tissue foreign body response and tumor-associated enzymes.

The location of the nanorattle probes was tracked in vivo after intravenous injection in a transgenic CX3CR1-EGFP/FLK1-mCherry mouse with an intact immune system. Stability of the nanorattle probes after circulation in the bloodstream is extremely important for targeted delivery and for use as contrast agents and/or sensing probes. To confirm the accumulation of SERS probes in the tumor present in a window chamber, two photon luminescence (TPL) was performed of nanorattles in the live mouse prior to the SERS measurements. After 24 hrs of in vivo circulation in the immune competent mouse, the animal organs were harvested and the SERS signals were measured from the harvested tumor, kidney, heart, spleen, liver, and skin. No detectable SERS signal was found in the blood, which indicates the nanorattles were eliminated from the blood circulation and accumulated in the spleen and tumor after 24 hrs. FIG. 10A shows SERS signals of intravenously injected nanoprobes in immune competent mouse after 24 hrs. Strong SERS signals were detected in both tumor and spleen, which indicated the SERS nanorattle probes were not affected by the immune competent mouse. FIG. 10B shows the immune responsive mouse with Lewis Lung Carcinoma (LLC) tumor in a dorsal window chamber. FIG. 10C shows in vivo two photon luminescence of TARGETs obtained from the tumor location after 24 hrs of circulation, which indicates that TARGETs accumulated in the tumor due to its leaky vasculature.

In some embodiments, the present disclosure provides systems, methods and instrumentation for use with the nanorattles that are ultra bright, tunable, stable and have an internal standard signal for in vivo and in vitro diagnostic and therapeutic applications. The improved features of the nanorattles of the present disclosure include: 1) ultrabright SERS signals that can be tuned over a large spectral range; 2) multiple dyes can be loaded into the nanorattle gap structures; 3) the nanorattles can serve as a stable internal and external standard under harsh in vivo and in vitro systems; 4) the nanorattles can be integrated with nucleic acid probes for detecting nucleic acids including, but not limited to, inverse molecular sentinel (iMS) nanorattle probes for in vitro and in vivo sensing; 5) the nanorattles can be integrated with magnetic particles and plasmonics coupling interferences system; 6) the nanorattles can be integrated with magnetic particles for nucleic acid target detection, concentration, separation, and sensing; 7) the nanorattles can be integrated with magnetic particles for protein (or small molecule) target detection, concentration, separation, capture using antibodies (or aptamers), and sensing.

In some embodiments, compositions and methods are provided for improved DNA, RNA and protein-based diagnostic technologies including: 1) plasmonic coupling enhancement (PCE) to achieve ultra-bright multiplex SERS nanoprobes (>1000 stronger than SERS-based nanosphere probes); and 2) a synthetic approach for preparing the nanorattles of the present invention that includes a combination of galvanic replacement and seed mediated growth to load Raman reporter molecules into a gap between the core and shell of the nanorattle and close the pores created by the galvanic replacement to prevent reporter degradation under harsh conditions, such as, for example in vivo; 3) precise tuning of nanoparticle core-shell gap width, core size, and shell thickness to modulate the plasmonic effect and to achieve a maximum electric-field (E-field) intensity at desirable wavelengths; 4) a seamless combination of DNA hybridization and magnetic separation with ultrasensitive SERS detection; and 5) a method that does not require sample amplification (e.g., PCR).

Additional advantages of the present invention include: methods and use of the nanorattles to provide internal standard SERS signal for nucleic acid probes including the molecular sentinel and inverse molecular sentinel nucleic acid probes; and methods and use of the nanorattles for protein targets including anti-biofouling properties.

Further advantageous nanorattle compositions and uses thereof, include multiple nanorattle structures for different plasmonics activation regimes (e.g., NIR, MW, Ultrasound etc); nanoparticles having multilayered nanoshells; nanorattles having a dielectric nanoparticle core covered with a metal nanocap; nanorattles having a shell covering a dielectric spheroid core; nanorattles having an oblate metal nanoshell covering a dielectric spheroid core; nanorattles having a metal nanoparticle core covered with dielectric nanoshells; nanorattles having a protective coating layer; nanorattles having multi-layer metal nanoshells covering a dielectric spheroid core; nanorattles having multi-nanoparticle structures; nanorattles having metal nanocube and nanotriangle/nanoprism; nanorattle probes using a metal cylinder; nanorattles including metal nanostars; nanorattles capable of multiplex detection.

In further embodiments, advantages and uses of the nanorattle compositions and uses thereof include: nanorattles having bioreceptors (antibodies, proteins, cell receptors, aptamers etc) and methods of use thereof; nanorattles for methods using nanoparticle delivery systems; nanorattles and use thereof for methods combining plasmonics photospectral properties, biocompatibility, improved nanoparticle payload delivery and passive targeting of gold nanoparticles; nanorattles and methods of use thereof with liposomes; nanorattles and methods of use thereof for two-photon or multi-photon excitation; nanorattles and methods of use thereof in the electromagnetic spectrum ranging from gamma rays and X rays throughout ultraviolet, visible, infrared, microwave and radio frequency energy for excitation; nanorattles and methods of use thereof for multiplex detection; nanorattles and methods of use thereof for multispectral imaging for multiplex detection; and nanorattles and methods of use thereof for color change for rapid diagnostics.

In one embodiment, a portable in vivo diagnostic system is provided for use with the nanorattles of the present invention. The portable in vivo diagnostic system can include a pocket-sized or palm-sized in vivo diagnostic system. In one embodiment a wrist-watch-sized in vivo diagnostic system for use with the nanorattles is provided.

In further embodiments, the nanorattle probes can be applied to applications based on DNA/RNA/protein detection including point-of-care diagnostics, food safety, environmental monitoring, quality control applications, and homeland defense.

The combination of galvanic replacement and the seed mediated growth method was employed to load Raman reporter molecules and subsequently close the pores to prevent leaking and degradation of reporters under physiologically extreme conditions. Precise tuning of the core-shell gap width, core size, and shell thickness allows us to modulate the plasmonic effect and achieve a maximum electric-field (E-field) intensity. The interstitial gap of TARGET nanoprobes can be designed to exhibit a plasmon absorption band at 785 nm, which is in resonance with the dye absorption maximum and lies in the "tissue optical window", resulting in ultra-bright SERS signals for in vivo studies. The results of in vivo measurements of TARGETs in laboratory mice illustrated the usefulness of these nanoprobes for medical sensing and imaging.

In one embodiment, a method is provided for using the nanorattles for detecting nucleic acid targets. In one example depicted in FIG. 11, two silver or gold nanorattles are provided, each having a SERS dye embedded inside the interstitial core-shell gap and having an attached probe DNA sequence. The $1^{st}$ nanorattle probe (which has a SERS dye embedded inside the interstitial core-shell gap) has a DNA sequence identical to the half target sequence of interest and has a Raman label bound at the end of the probe. The $2^{nd}$ nanorattle probe (which has a SERS dye embedded inside the interstitial core-shell gap) has a DNA sequence identical to the other half target sequence of interest and has a Raman label bound at the end of the probe.

Figures 11A, 11B:
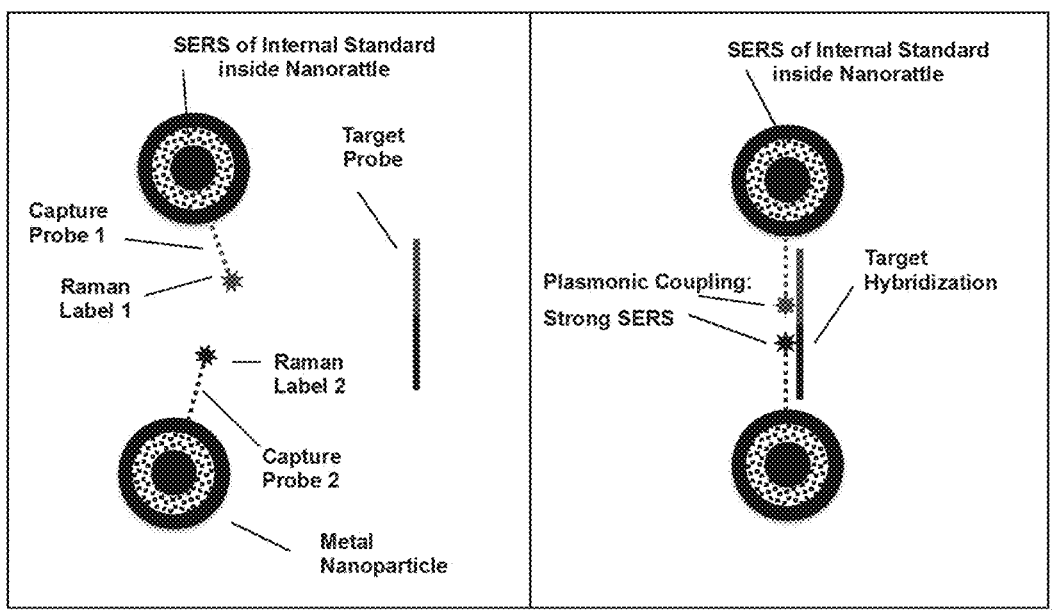
FIG. 11A is a schematic diagram illustrating the use of two nanorattle probes for monitoring and quantitatively detecting target DNA/RNA and, at the same time, using the SERS signal of the dye inside the nanorattle as an internal standard and shows the two separate nanorattle probes, each having a capture probe with an attached Raman label, and a separate target nucleic acid probe.
FIG. 11B is a schematic diagram illustrating the use of two nanorattle probes for monitoring and quantitatively detecting target DNA/RNA and, at the same time, using the SERS signal of the dye inside the nanorattle as an internal standard and shows the two separate nanorattle probes of FIG. 11A brought into close proximity due to hybridization with the target nucleic acid probe, which results in plasmonic coupling and strong SERS.

When these two types of nanorattle probes are mixed with the target sequence, they hybridize to the target sequence in such a way that the SERS labels are in the middle (FIG. 11B). As a result the two Raman labels are "trapped" between the two nanorattles. Due to interparticle plasmonics coupling, upon excitation (e.g., using a laser or other appropriate energy sources) of the Raman label molecules, the electromagnetic enhancement of the Raman signal is very intense, leading to extremely strong SERS signals of the two Raman label (FIG. 11B). The increase of the SERS signal intensities of the two Raman labels can be used as a parameter for monitoring and quantitatively detecting the target DNA/RNA in the assay. At the same time, the SERS signal of the dye inside the nanorattle can be used as the internal standard.

In one embodiment, a kit is provided for the detection of a nucleic acid target molecule, comprising: a first nanorattle having: 1) an essentially spherical gold metal nanoparticle core, 2) a porous material of an essentially uniform width surrounding the nanoparticle core comprising silver metal and one or more SERS reporter molecules, and 3) an outer gold metal shell encapsulating the porous material, wherein the first nanorattle comprises an attached first oliognucleotide sequence complementary to a first portion of the nucleic acid target (Capture probe 1), wherein the oliognucleotide sequence comprises a first bound Raman label 1; and a second nanorattle having: 1) an essentially spherical gold metal nanoparticle core, 2) a porous material of an essentially uniform width surrounding the nanoparticle core comprising silver metal and one or more SERS reporter molecules, and 3) an outer gold metal shell encapsulating the porous material, wherein the second nanorattle comprises an attached second oliognucleotide sequence complementary to a second portion of the nucleic acid target (Capture probe 2), wherein the oliognucleotide sequence comprises a second bound Raman label 2.

Figures 12A, 12B, 12C:
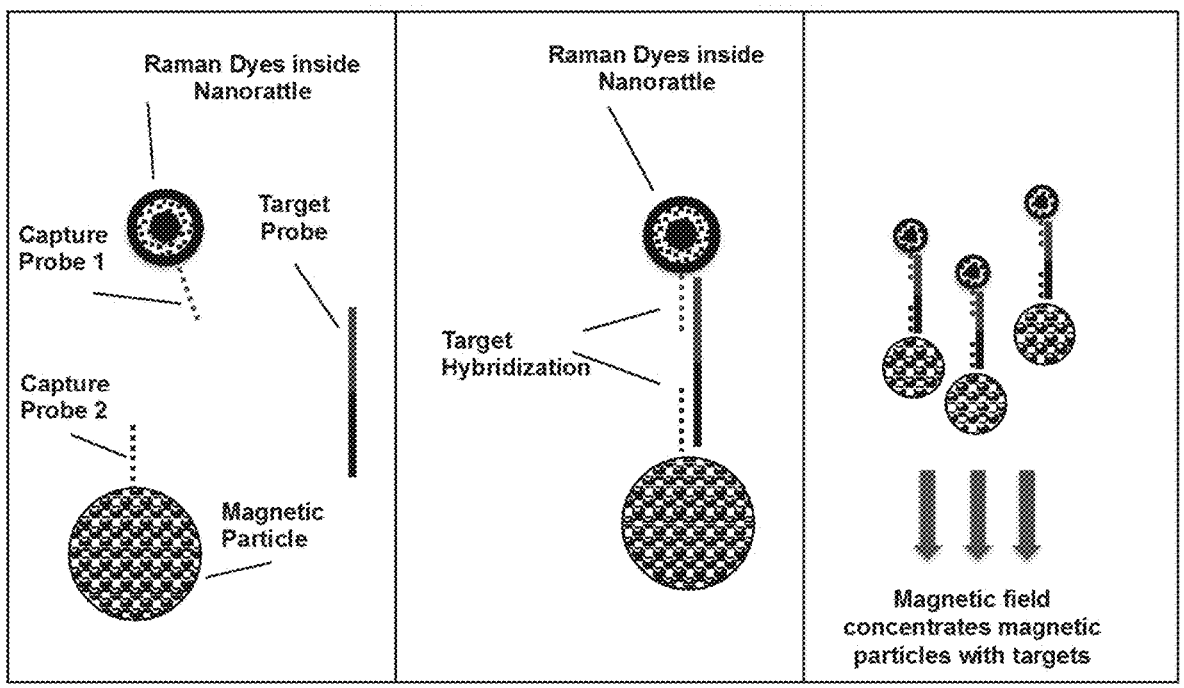
FIG. 12A is a schematic diagram illustrating the use of nanorattle probes in a sandwich hybridization of magnetic beads for concentration of nucleic acid molecules and shows a magnetic particle and a SERS nanorattle, each having an attached capture probe, and a separate target sequence (Target Probe)
FIG. 12B is a schematic diagram illustrating the use of nanorattle probes in a sandwich hybridization of magnetic beads for concentration of nucleic acid molecules and shows the magnetic particle and the SERS nanorattle of FIG. 12A upon hybridization to the target sequence to form a hybridization sandwich (FIG. 12B).
FIG. 12C is a schematic diagram illustrating the use of nanorattle probes in a sandwich hybridization of magnetic beads for concentration of nucleic acid molecules and shows a magnetic field being applied to concentrate the hybridization sandwiches of FIG. 12B at a detection spot for SERS measurements.

In one embodiment of the invention, a sensitive yet simple DNA detection method is provide using the ultrabright SERS nanorattles. First, nanorattles and magnetic microbeads are functionalized with gene reporter probes and gene capture probes, respectively. The two probes are designed to be complementary to the two ends of the target sequences. Second, the functionalized nanorattles and magnetic microbeads are mixed with sample solutions of interest (FIG. 12A). In the presence of the target sequences, hybridization sandwiches of magnetic bead-target sequence-nanorattle are formed (FIG. 12B). Third, a magnet is used to concentrate the magnetic bead-target sequence-nanorattle sandwiches onto a small spot for detection (FIG. 12C). This technology, has several major advantages: 1) highly sensitive without amplification by employing ultrabright SERS nanorattles as labels and removing all captured targets from a complex samples; 2) highly specific by employing nucleic acid hybridization; 3) capable for multiplex detection targets in a single reaction using nanorattles with different "colors"; and 4) sample-to-answer capability by combining sample preparation, target separation, and target detection using magnetic microbeads. The addition of target DNA with complementarity to both reporter and capture probes creates a specific and sensitive hybridization sandwich.

Figure 13A:
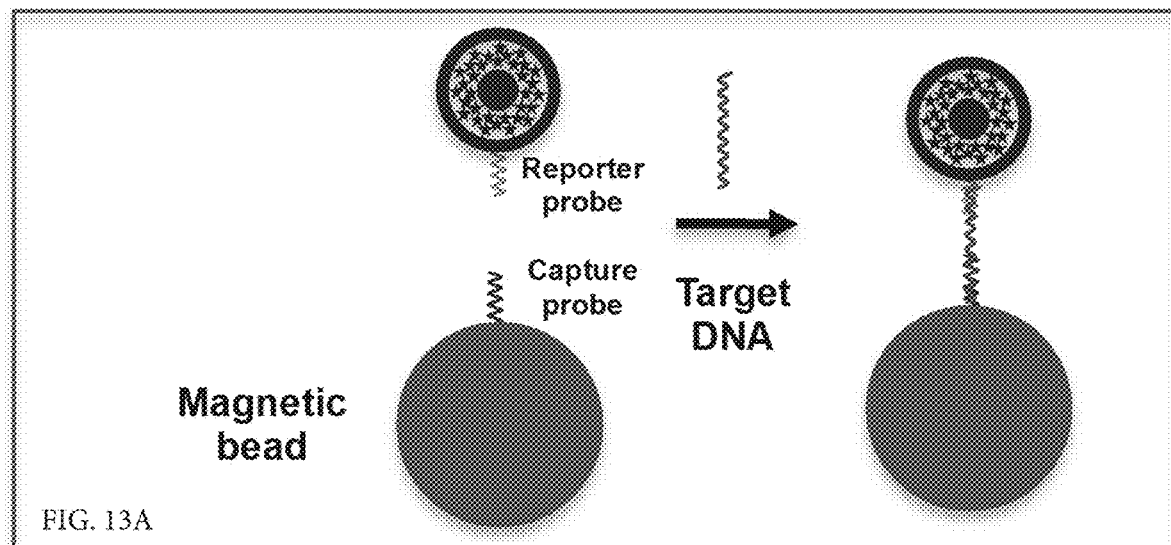
FIG. 13A shows a nanorattle-based DNA detection method using sandwich hybridization and shows (1) a magnetic bead loaded with capture probes, (2) a target sequence, and (3) an ultrabright SERS nanorattle loaded with reporter molecules.
Figure 13B:
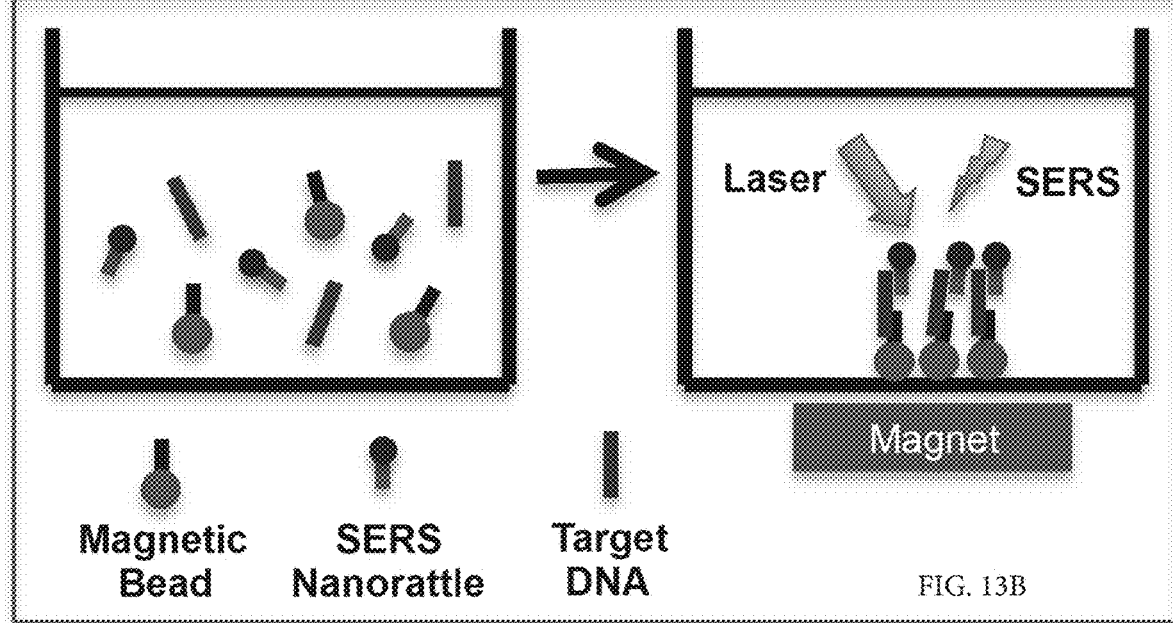
FIG. 13B shows a nanorattle-based DNA detection method using sandwich hybridization and shows a magnet is applied to concentrate the hybridization sandwiches at a detection spot for SERS measurements.

In one embodiment, the detection scheme of the nanorattle-based method is shown in FIG. 13. Magnetic beads and nanorattles are functionalized with DNA capture probes and DNA reporter probes, respectively. The two probes are designed to be complementary to the two ends of the target sequences. Detection is conducted by subsequently adding to sample solutions of interest magnetic beads that are loaded with capture probes and nanorattles that are loaded with reporter probes. In the presence of the target sequences, hybridization sandwiches of magnetic bead-target sequence-nanorattle are formed (FIG. 13A). A magnet is used to concentrate the magnetic bead-target sequence-nanorattle sandwiches onto a small spot for SERS measurement (FIG. 13B).

Using the methods of the present disclosure, a specific DNA sequence of the malaria parasite *Plasmodium falciparum* is detected with a detection limit of approximately 100 attomoles (FIG. 14). Single nucleotide polymorphism (SNP) discrimination of wild type malaria DNA and mutant malaria DNA, which confers resistance to artemisinin drugs, was also demonstrated. The results are shown in FIG. 14. SERS intensity was high when *P. falciparum* wildtype target sequences were added, owing to the complementarity between probe and target sequences. In contrast, after the addition of a *P. falciparum* mutant sequence, the SERS intensity was low, owing to a single-based pair mismatch which allows the unstable double strands to dehybridize and thereby attenuate SERS intensity. For the non-falciparum sequence and blank, SERS intensities were close to zero.

Figures 15A, 15B:
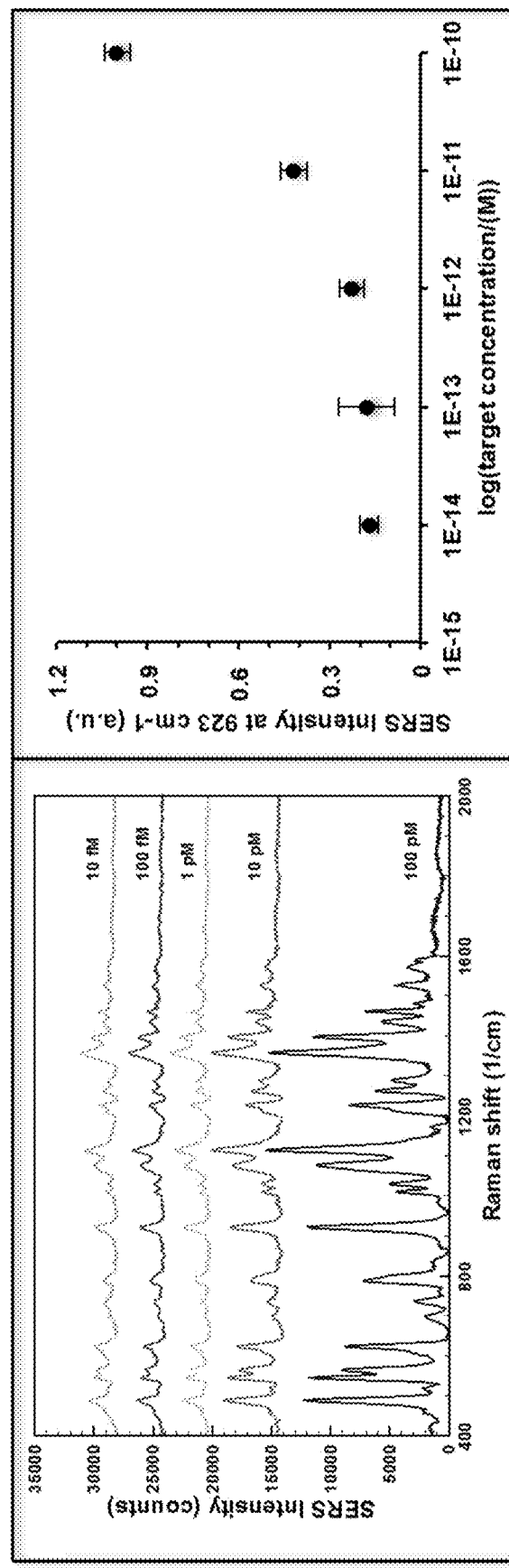
FIG. 15A shows SERS nanorattle detection of wild type P. falciparum DNA and is a graph showing SERS spectra at different concentrations of wild type target P. falciparum gene PF3D7_1343700 (vertically shifted for clarity).
FIG. 15B shows SERS nanorattle detection of wild type P. falciparum DNA and is a graph showing SERS intensities at 923 cm$^{-1}$ (normalized) vs. log(target concentration/(M)). Error bars represent standard deviations (n=3).

In addition, the sensitivity of the nanorattle-based technique was quantified by testing samples of the *P. falciparum* wildtype target sequence at different concentrations (FIG. 15A-15B). The results indicated that the current unoptimized nanorattle-based technique could detect malaria (*P. falciparum* wildtype target sequence) at 100 femtomolar concentration range. By considering the signal-to-noise ratio values, the limit of optical detection (LOD) is estimated at 10 femtomolar concentration even without having optimized the experimental conditions. Since only 20 µL samples were used, the absolute LOD is 200 zeptomoles ($2\times10^{-19}$ moles) of the malaria target.

Thus, in one embodiment a nucleic acid detection method is provided based on sandwich hybridization of magnetic bead, target sequence, and ultrabright SERS nanorattle. The nanorattle has a core-gap-shell structure with Raman reporters loaded in the nanosize gap between the core and the shell. The nanorattles can be more than three orders of magnitude brighter than gold nanospheres loaded with the same Raman reporter. The nanorattle can be used as a SERS tag for nucleic acid detection using sandwich hybridization and magnetic beads. The detection limit can be approximately 100 attomoles or less for gene targets including, but not limited to, *P. falciparum* DNA targets. Discrimination between a wild type and a SNP mutant of a gene, including but not limited to a *P. falciparum* gene sequence can be accomplished with this method. The presented method is simple, sensitive, and suitable for automation, making it an attractive candidate for integration into portable platforms for POC molecular diagnostics.

These test models demonstrate the molecular diagnostic potential of the nanorattle-based method to both detect and genotype infectious pathogens. Furthermore, the method's simplicity makes it suitable for integration into portable platforms for Point of Care (POC) and in resource-limited settings applications.

In some embodiments, the nanorattle probes can be used in various bioassays where the nanorattle functions as an internal standard. FIG. 16 illustrates the different uses of the nanorattle probes with the nanorattle as internal standard in various bioassays. FIG. 16A shows bioassays using antibody probes. Nanorattles [with dye(s) in interstitial gap] and having an antibody bioreceptor. The bioreceptor captures the target antigen that exhibits SERS when it gets close the metal surface of the nanoprobe. The nanorattle provides the internal standard SERS signal.

In another embodiment, the presence of target species (e.g., protein, etc) with affinity to both reporter and capture antibodies creates a specific and sensitive assay. Then a magnet can be used to concentrate the magnetic bead-target nanorattle sandwiches onto a small spot for detection. At the same time the SERS signal of the dye inside the nanorattle can be used as the internal standard.

FIG. 16B shows bioassays using nucleic acid probes. In this embodiment, the nanorattle [with dye(s) in interstitial gap] and also includes an attached Inverse Molecular Sentinel (iMS) probe. Upon target nucleic acid (DNA, mRNA, miRNA) hybridization to the capture probe of the iMS, the iMS forms a stem loop leading to a SERs signal. The nanorattle provides an internal standard SERS signal.

FIG. 16C shows bioassays using aptamer probes. In this embodiment, the nanorattle [with dye(s) in the interstitial gap] includes an attached aptamer probe. The aptamer captures the target protein or small molecule, which causes the Raman label to move in closer to the metal surface of the nanorattle, leading to strong SERS. The nanorattle provides an internal standard SERS signal.

Figures 17A, 17B:
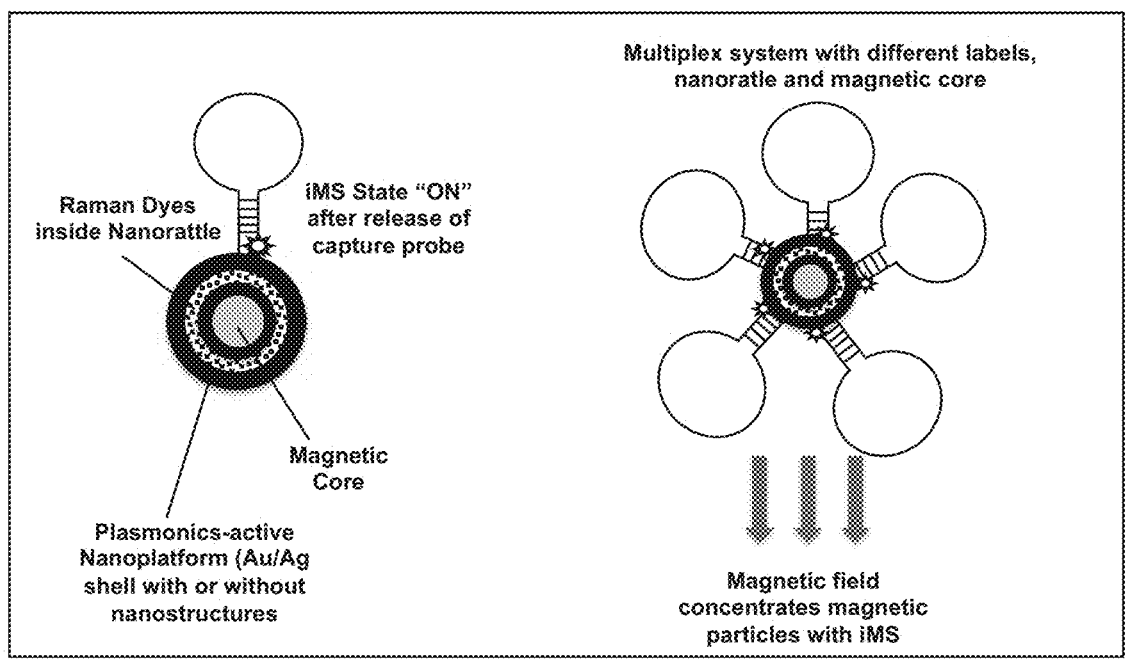
FIG. 17A is a schematic diagram showing probe designs that include a nanorattle using an inverse Molecular Sentinel (iMS) scheme and shows a nanorattle with a single iMS.
FIG. 17B is a schematic diagram showing probe designs that include a nanorattle using an inverse Molecular Sentinel (iMS) scheme and shows a nanorattle with multiple iMS molecules.

In some embodiments, a probe design is provided with a nanorattle using the inverse Molecular Sentinel (iMS) scheme (FIG. 17) [For MS and iMS See also: T. Vo-Dinh, "SERS Molecular Probe for Diagnostics and Therapy and Methods of Use Thereof", U.S. Pat. No. 7,951,535 (2011); T. Vo-Dinh, A. Fales and H, N. Wang, "Nano-Plasmonic Molecular Probes, U.S. Patent pending," DU4103; PCT/US2013/059312]. FIG. 17 is a schematic diagram showing probe designs that include a nanorattle using an inverse Molecular Sentinel (iMS) scheme. FIG. 17A shows a nanorattle with a single iMS. FIG. 17B shows a nanorattle with multiple iMS molecules. Here the SERS signal of the dye inside the nanorattle can be used as the internal standard. Magnetic bead pull-down allows sample separation, concentration and SERS detection.

Figure 18:
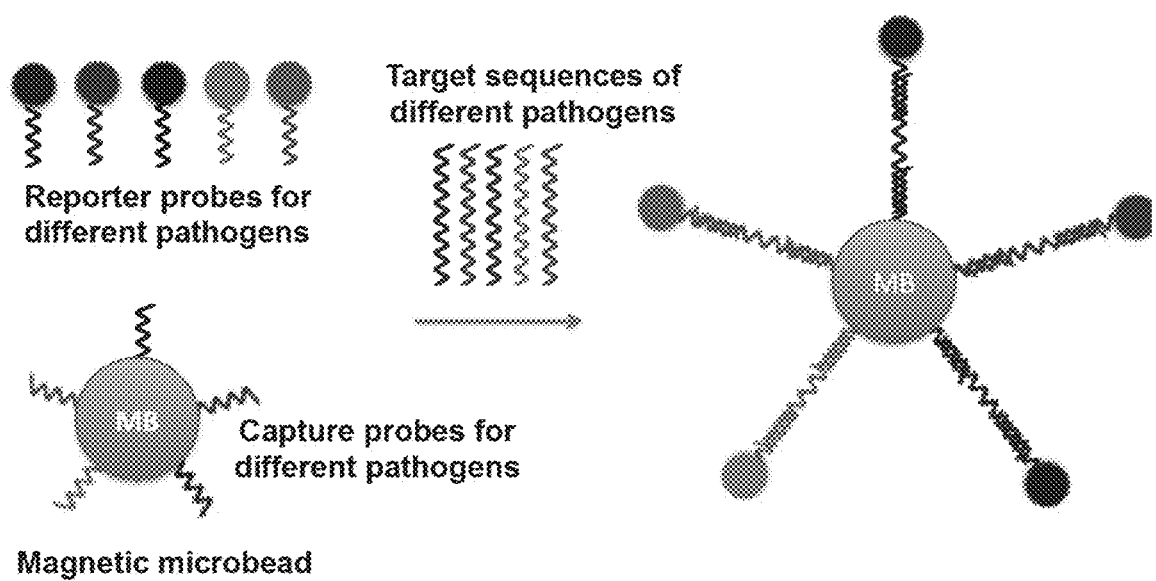
FIG. 18 illustrates a schematic structure of multiplexed SERS nanorattles loaded with DNA capture probes for simultaneous detection of multiple gene targets. A single magnetic bead is annealed with capture oligo probes. The addition of reporter probes and target oligos bridges bead and reporter, allowing for bead pull-down and SERS detection.

In some embodiments, multiplexed SERS nanorattles are provided that are loaded with DNA capture probes for simultaneous detection of multiples gene targets. FIG. 18 illustrates a schematic structure of multiplexed SERS nanorattles loaded with DNA capture probes for simultaneous detection of multiple gene targets. A single magnetic bead is annealed with capture oligo probes. The addition of reporter probes and target oligos bridges bead and reporter, allowing for bead pull-down and SERS detection.

In one embodiment, a kit is provided for the detection of a nucleic acid target molecule, comprising: a nanorattle having: 1) an essentially spherical gold metal nanoparticle core, 2) a porous material of an essentially uniform width surrounding the nanoparticle core comprising silver metal and one or more SERS reporter molecules, and 3) an outer gold metal shell encapsulating the porous material, wherein the nanorattle comprises an attached oliognucleotide sequence complementary to a first portion of the nucleic acid target (Reporter probe); and a magnetic bead, wherein the magnetic bead comprises an attached oliognucleotide sequence complementary to a second portion of the nucleic acid target (Capture probe).

In one embodiment, a method is provided of detecting a biological target molecule, the method comprising: contacting a nanorattle consisting essentially of: 1) an essentially spherical gold metal nanoparticle core, 2) a porous material of an essentially uniform width surrounding the nanoparticle core comprising silver metal and one or more SERS reporter molecules, and 3) an outer gold metal shell encapsulating the porous material, and further comprising an attached bioreceptor for the biological target molecule selected from the group consisting of: an antibody, a nucleic acid, a peptide, an aptamer, a molecular sentinel (MS), and an inverse molecular sentinel (iMS), with a sample of interest under conditions suitable for binding of the bioreceptor to the target molecule, to detect one or a combination of a presence, an absence, or a concentration of the target molecule in the sample.

Figure 19A:
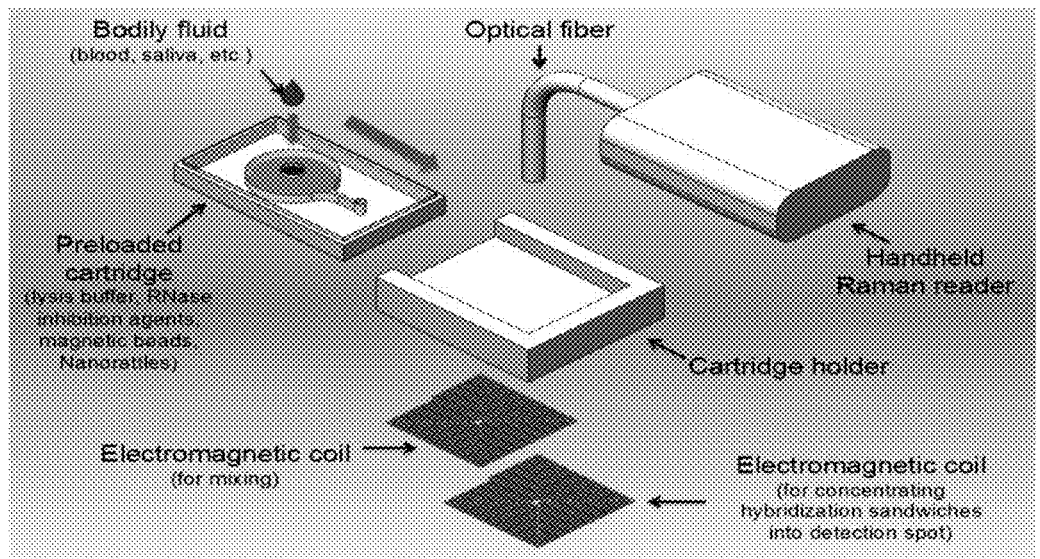
FIG. 19A shows a schematic of an integrated diagnostics system for use with the nanorattles in which all of the following are integrated into a single platform: (1) sample pre-treatment, (2) target separation and concentration using magnetic beads, and (3) ultrasensitive multiplex detection. Bodily fluid samples can be delivered directly into the chamber of a pre-loaded cartridge with no sample prep and shows an exploded view of the integrated diagnostics system.
Figure 19B:
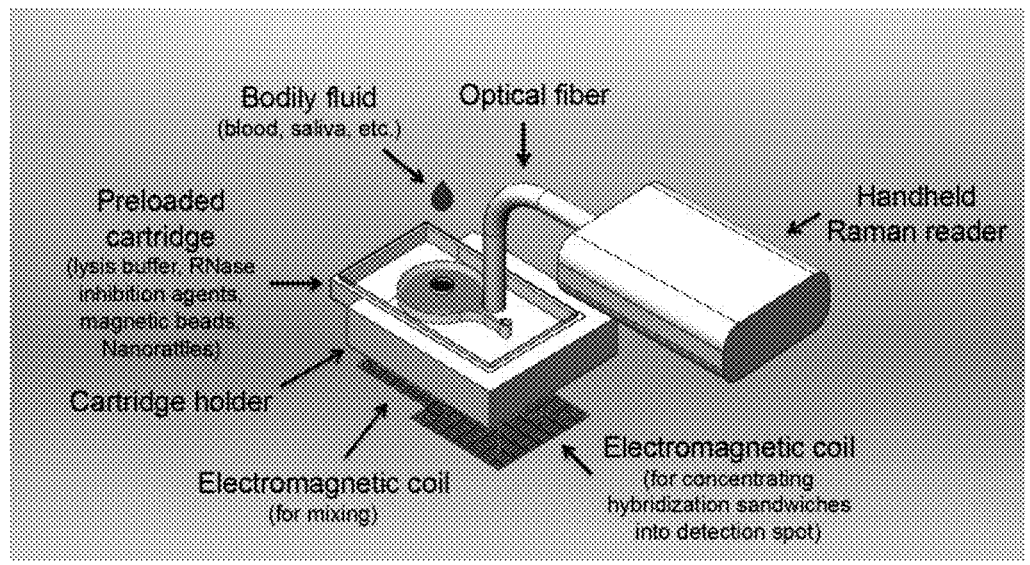
FIG. 19B shows a schematic of an integrated diagnostics system for use with the nanorattles in which all of the following are integrated into a single platform: (1) sample pre-treatment, (2) target separation and concentration using magnetic beads, and (3) ultrasensitive multiplex detection. Bodily fluid samples can be delivered directly into the chamber of a pre-loaded cartridge with no sample prep and shows the assembled view of the integrated diagnostics system.

In some embodiments, integrated diagnostics systems including the nanorattles are provided for in vitro applications. The integrated diagnostics systems integrate all of the followings into a single platform: (1) sample pre-treatment, (2) target separation and concentration using magnetic beads, and (3) ultrasensitive multiplex detection. Bodily fluid samples can be delivered directly into the chamber of a pre-loaded cartridge with no sample prep (FIG. 19A-B). The pre-loaded cartridge contains the lysis buffer, RNase inhibitors, magnetic beads functionalized with capture probes, and nanorattles functionalized with reporter probes for rapid sample pre-treatment and target detection. First, the samples are lysed by the lysis buffer. Nucleic acid content are released into the solution and captured by the magnetic beads and nanorattles to form sandwiches of magnetic bead-target sequence-nanorattle. RNase inhibitors prevent RNase from degrading the released RNA. The Electromagnetic Coil (EMC 1) is used for mixing magnetic beads, thus increasing capture efficiency. Second, the Electromagnetic Coil (EMC 2) is then used to concentrate the sandwiches of magnetic bead-target sequence-nanorattle to the detection site under an optical fiber (FIG. 19A-B). Here, SERS signals are measured directly using a compact handheld Raman reader coupled the other end of the fiber. By using nanorattles with different colors, a multiplex diagnostic system with "sample-in-answer-out" capability can be achieved.

In some embodiments, the nanorattles of the present disclosure can be used for in vivo diagnostics applications. A challenge for many real-life applications is the development of SERS nanoprobes that are highly stable under harsh physiological conditions often encountered in in vivo measurements. To achieve these critical properties required for biomedical imaging and sensing, several SERS nanoprobes have been previously developed by adsorbing and conjugating Raman reporters on metal nanostructures and doping the Raman reporter in a porous silica shell. However, in this invention the APN nanoprobe achieve these critical properties while also improving the stability of the reporters in vivo-protecting them in a solid shell. Also the nanorattles can provide SERS signal for use as internal standards.

The nanorattles can be linked to or integrated within biosensing nanoprobes. The nanorattle probes can be deposited under the skin to form a 'smart mole' that can monitor target in tissue or in the blood stream. The nanorattle probes having magnetic cores can be moved to and concentrated in an area suitable for detection. Alternatively the nanorattle probes can also be attached to a biocompatible material inside the skin layer.

Several diagnostics systems are possible, depending on the degree of miniaturization. Detection of the target can use a portable Raman diagnostic system having excitation light source and an optical detector. An alternative diagnostic system consists of a pocket-sized (or palm-sized) battery-operated Raman diagnostics system that is linked to the 'smart mole' by fiberoptics excitation and detection. The pocket-sized system can be operated remotely by an iPhone or similar device. Further miniaturization can shrink the size of the portable diagnostic system into the size of a 'wristwatch-sized' battery-operated Raman diagnostics device.

EXAMPLES

The following Examples have been included to provide guidance to one of ordinary skill in the art for practicing representative embodiments of the presently disclosed subject matter. In light of the present disclosure and the general level of skill in the art, those of skill can appreciate that the following Examples are intended to be exemplary only and that numerous changes, modifications, and alterations can be employed without departing from the scope of the presently disclosed subject matter.

Example 1

Synthesis of Nanorattles

Materials. All materials were used as received without any further purification. Cetyltrimethylammonium bromide (CTAB), gold chloride ($HAuCl_4.4H_2O$) solution, sodium borohydride (NaBH4), ascorbic acid, sodium chloride (NaCl), polyvinylpyrrolidone (PVP (58000 MW)), 1-tetradecanol, cetyltrimethylammonium chloride (CTAC) solution (25 wt % in $H_2O$) were obtained from SIGMA-ALDRICH (St. Louis, Mo., USA). Silver nitrate ($AgNO_3$, 99.995%) was purchased from ALFA AESAR (Ward Hill, Mass.). MEBM (Mammary Epithelial Basal Medium) medium and MCF-10A cell line were obtained from the Duke University Cell Culture Facility (Durham, N.C.). The FORMVAR/carbon-coated copper TEM grids were purchased through VWR (RADNOR, Pa.).

Synthesis of gold nanoparticles (AuNP). Gold nanoparticles were synthesized using a previously reported method. Seed solution was prepared by vigorous mixing of 10 ml of aqueous CTAC solution (0.1 M), and 250 µl of $HAuCl_4$ (10 mM) with 450 µl of ice-cold $NaBH_4$(10 mM) solution. The seed solution was aged for 2 hrs at room temperature (25° C.). In a separate vial, the growth solution was prepared in 10 ml of aqueous CTAC solution (0.1M), 250 µl of $HAuCl_4$ (10 mM), and 25 µl of ascorbic acid (0.1M). To this colorless solution, 25 µl of seed solution was added with vigorous stirring and kept undisturbed overnight to obtain highly uniform spherical nanoparticles that exhibit a Localized Surface Plasmon Resonance (LSPR) at 518 nm. The diameter of the nanoparticles obtained at this stage was ~20 nm.

Synthesis of a silver shell surrounding the AuNPs: A silver shell was grown around gold nanostructures (18 nm) (AuNP) (see FIG. 4A). To grow the silver shell on AuNP, polyvinylpyrrolidone (PVP) was employed as the stabilizing agent. Silver nitrate ($AgNO_3$) solution (5 mM) was added to the above mixture and stirred vigorously for 10 s. The reaction solution was left undisturbed for 2-3; days to allow the formation of AuNP@Ag nanostructures at room temperature. The size of the silver shell was adjusted by changing the amount of precursor AuNPs seeds or by changing amount of $AgNO_3$ solution.

In an alternative method, a silver shell coating on gold nanoparticles (AuNP@Ag) is accomplished using the following method: Gold nanoparticles were centrifuged once (13000 rcf, 15 min) and resuspended in 1 mM PVP 55K. The above solution (48 ml) was mixed with 144 ml 1 mM PVP 55 k and 38.4 ml 0.1 M CTAC under magnetic stirring. After that, 200 microliter 0.2 M AgNO3 was added. The solution was aged for 10 min followed by addition of 10 ml 0.1M ascorbic acid. A total 5.2 ml 0.25 M NaOH was then added dropwise. During NaOH addition, the solution color slowly changes from wine red to orange color, indicating the formation of a silver shell on the AuNP core (AuNP@Ag). The magnetic stir was turned off and the solution was left undisturbed for several hours.

Synthesis of cage-like nanoparticles. Galvanic replacement reaction was employed to transform the silver shell on AuNP into a porous gold shell (AuNP@Cage). Specifically, the AuNP@Ag solution was centrifuged for 10 min at 8000 rpm and suspended in 1-mM PVP solution. The PVP-modified AuNP@Ag solution was brought to boil by heating to 100° C. $HAuCl_4$ (1 mM) solution was added to the AuNP@Ag's, while the solution was constantly stirred. Addition of gold salt was stopped once the solution turned a vibrant blue/purple color to indicate formation of the (AuNP@Cage).

Loading of reporter molecules into the cage-like nanoparticles: The porous nanoparticles obtained according to the procedure above were centrifuged two times at 8000 rpm and redispersed in a mixture of 2-[7-(1,3-dihydro-1,3,3-trimethyl-2H-indol-2-ylidene)-1,3,5-heptatrienyl]-1,3,3-trimethyl-3H-indolium iodide (HITC) (or Methylene Blue/Rose Bengal)(0.1 mM) and 1-tetradeconol (10 mg) in 200 µl of ethanol at ~100° C. (see FIG. 4A). The reaction was allowed to proceed for 1 hr to evaporate most of the ethanol and dispersed in ice cold water to solidify the reporter dye inside the porous nanoparticle. The solidified 1-tetradeconol at low temperature (4° C.) was slowly separated from nanoparticles in water using 1 ml pipette. Then the nanoparticle solution was centrifuged 3-5 times to completely remove the trace reporter dye molecules. The detailed procedure to load dyes and drugs is available in previous reports.

Synthesis of nanorattles having an outer gold shell: To form the outer gold shell on the nanoparticles loaded with the resonance Raman reporters described above, a seed-mediated growth method was employed (see FIG. 4A). Briefly, a gold shell on the nanoparticles was synthesized using 10 ml of growth solution containing 4.5 mM $HAuCl_4$ and 1 ml of 0.1 M ascorbic acid. Then 1 ml of 1-nM porous nanoparticles loaded with reporter molecules was added to the above growth solution and stirred vigorously for 10 sec. The reaction mixture was left undisturbed (overnight) to form an essentially uniform solid shell. The formation of this shell was confirmed by both TEM and UV/Vis analysis (see FIGS. 4B and 5B-5F).

Nanorattle size. The size and concentration of the nanorattles were measured using the nanoparticle tracking analysis (NTA) option available in the NANOSIGHT NS500 device. The graph shown is FIG. 9 is the size and concentration of the nanorattles diluted 1000 fold from the original concentration after synthesis.

Example 2

Tunable Raman Gold Nanoprobes for in Vivo Sensing and Imaging

In vivo procedures: Mouse window chamber surgeries were performed as described in a reported protocol. Briefly, nude mice were anesthetized with a 100 mg/kg and 10 mg/kg, ketamine/xylazine mixture by an intraperitoneal injection and underwent surgery for placement of a dorsal skin window chamber using sterile surgical procedures. A 12-mm diameter flap of skin was dissected away from the front surface of the dorsal skin flap, leaving the opposite fascial plane with its associated vasculature intact. Following skin-fold dissection, a pair of titanium window frames were mounted and sutured to the skin flap. $1\times10^5$ Lewis Lung Carcinoma (LLC) cells were injected into the center of the window region beneath the fascial plane, and a cover glass was placed over the area of incision. All mice received an injection of 0.05-mg/kg buprenorphine subcutaneously following surgery. Mice were imaged 10 days after surgical implantation of the window chamber to allow time for tumor development. The nanoparticle solution (100 µL of 1 nM) was administered to the animals via tail vein injection. After 24 hours, two-photon imaging was performed on animals anesthetized using a ketamine/xylazine mixture as previously described. Animals were awake and restrained by hand during SERS imaging measurements. Following imaging, mice were euthanized with 0.05 mL of euthasol (sodium pentobarbital 390 mg/ml with sodium phenytoin 50 mg/ml). Tumor, skin sample, liver, spleen, heart, and kidneys were immediately harvested and placed on ice. All animal procedures were carried out with approval from the Institutional Animal Care and Use Committee (IACUC) at Duke University.

Tuning the nanorattle gap between core and shell versus SERS. FIG. 7 shows TEM images of HITC molecules trapped in nanorattles with 10 nm (A), 5 nm (B), and 2 nm (C) gaps between core and shell. FIG. 7D shows SERS of the nanorattles with 10 nm, 5 nm, and 2 nm gaps. FIGS. 7E and 7F show Raman shift of corresponding nanorattless with 10 nm, 5 nm, and 2 nm gaps. These data clearly indicate there is significant upshift (12 cm$^{-1}$) in the case of 2 nm gap likely due to the molecular compression in narrow gap.

FIG. 8 shows TEM images and SERS of HITC present between the core and shell of the nanorattles with a 10 nm gap and a 10 nm thick shell in 3% $H_2O_2$ over time. There is no significant difference in SERS with and without $H_2O_2$ in first 30 min (as indicated by comparing No $H_2O_2$, 1 min, 5 min, 15 min, 30 min). However, after 24 hrs, the intensity of SERS significantly decreased mainly due to the formation of pores, complete etching of shell, and degradation of HITC in peroxide solution.

In vitro and In vivo stability of SERS probes. The in vitro stability of the SERS nanorattle probes in passively targeted breast epithelial cells (MCF 10A) was determined. SERS of HITC present in the nanorattles was highly stable even after 5 hrs and 24 hrs incubation, which indicates these probes are resistant to cellular enzymatic degradation. In addition, in vitro SERS mapping of nanoprobes at the single cell level was determined to confirm the successful internalization after passive targeting. In vivo SERS stability of the same nanorattles was analyzed in an immune compromised mouse having a tumor located in a window chamber. The nanorattles were injected directly into the tumor and the SERS signal was followed over time at the injection site. A fiber optic probe was used to excite the nanorattles (785 nm, 100 mW power) and the SERS signal was collected at the tumor location. SERS signal from the nanorattles was detectable even after 24 hrs following injection at the tumor site, which indicates these probes are not susceptible to tissue response and tumorigenic enzymes.

In vivo Sensing and Imaging. FIG. 9A shows SERS signals of intravenously injected nanorattle probes in an immune competent mouse after 24 hrs. Strong SERS signals were detected in both tumor and spleen, which indicated the SERS nanorattle probes were not affected by the immune competent mouse. FIG. 9B shows the immune responsive mouse with Lewis Lung Carcinoma (LLC) tumor in a dorsal window chamber. FIG. 9C shows the in vivo two photon luminescence of the nanorattles obtained from the tumor location after 24 hrs of circulation, which indicates that the nanorattles accumulated in the tumor due to its leaky vasculature.

Cell culture. Human epithelial breast cells (MCF-10A) were purchased from CCF at Duke University (Durham, N.C.) and sub-cultured in MEGM (MEBM mixed with a kit obtained from LONZA/CLONETICS CORP. Catalog No. CC-3150, which is optimized to grow the cells in serum free medium) as suggested by the AMERICAN TYPE CELL CULTURE protocol (Manassas, Va.). Cells were grown in an air-jacketed incubator at 37° C. with 5% $CO_2$-humidified atmosphere in 25 $cm^2$ tissue culture flasks. Once the cells reached 80-90% confluence, they were washed with phosphate buffered saline (PBS) and detached with 1 mL of 0.25% trypsin-EDTA solution (Sigma). The cells were dispersed in 10 ml MEGM medium and centrifuged at 800 RPM to completely remove trypsin. Cells were counted in a NEXCELON biosciences automated cell counter using cellometer cell counting chambers and seeded $4 \times 10^5$ cells per well (in three wells) in a 6 well plate.

In vitro SERS measurements. After 24 hrs, passively targeted MCF-10A cells with nanorattles were detached using 1 ml of 0.25% trypsin-EDTA and centrifuged at 800 RPM and redispersed in fresh complete medium. The detached cells were placed in cellometer cell counting chambers and incubated for 1 hr to attach partially to the surface of the plastic on the cell counting chamber. These cell counting chambers did not show any fluorescence or Raman background signal, which is important for SERS measurements. Then, Raman mapping with 1-micron spatial resolution was performed from single MCF-10A cells using a confocal INVIA RENISHAW Raman microscope with a 633-nm (10 mW) laser as the excitation source. The SERS signal from cells dispersed in medium was also measured after 24 hrs using a 785-nm laser to make sure the probes are stable over time.

In vivo two-photon luminescence (TPL) imaging: TPL imaging of nanorattles was performed using an OLYMPUS FV1000 multiphoton system containing a tunable femtosecond Ti-Sapphire laser (680-1080 nm). The focal volume of the objective lens (40×, 0.75 NA, water emersion) was used to scan along the Z-axis using a pair of gold-coated scanning mirrors. The mouse was anesthetized using a ketamine/xylazine solution (as described in the Methods section) and placed on a heated stage (WARNER INSTUMENTS). The TPL from nanorattles was collected using 800-nm excitation wavelength and Blue, Green and Red standard fluorescence cubes.

In vivo SERS sensing: In vivo SERS spectra were collected from the tumor region in the window chamber after nanorattle injection (100 ul of 1 nM). A 785-nm (100 mW) diode laser coupled with an INPHOTONICS fiber optic RamanProbe™ (Norwood, Mass.) was used for excitation. A fiber optic Raman probe is a device that uses fibers to deliver an excitation laser beam to a sample and collect the signal. SERS spectra was recorded using a PIXIS:100BReX CCD mounted to a LS-785 spectrograph (1200 grooves mm-1 grating), controlled by LIGHTFIELD software, from PRINCETON INSTRUMENTS (Trenton, N.J.). The collection fiber of the Raman probe was coupled to the entrance slit of the LS-785 spectrograph.

Example 3

Sensitive DNA Detection and SNP Discrimination Using Ultrabright SERS Nanorattles and Magnetic Beads Detection Scheme for Nucleic Acid Targets. The detection scheme of a nanorattle-based method for detecting nucleic acids is shown in FIGS. 11-13. In FIGS. 12 and 13, magnetic beads and nanorattles were functionalized with DNA capture probes and DNA reporter probes, respectively. The two probes are designed to be complementary to the two ends of the target sequences. Detection was conducted by subsequently adding to sample solutions of interest magnetic beads that are loaded with capture probes and nanorattles that are loaded with reporter probes. In the presence of the target sequences, hybridization sandwiches of magnetic bead-target sequence-nanorattle are formed. A magnet was used to concentrate the magnetic bead-target sequence-nanorattle sandwiches onto a small spot for SERS measurement.

Detection of Gene Targets. The nanorattle-based bioassay scheme depicted in FIGS. 11-13 was used and an assay designed to detect the P. falciparum gene PF3D7_1343700. A 53-base oligo of the wildtype PF3D7_1343700 and a complementary reporter probe were synthesized. To test the specificity of the designed probe, different samples composed of: wildtype PF3D7_1343700 sequence, the sequence with a single-base mismatch, non-malaria DNA, or blank were tested against the probe.

The results are shown in FIGS. 14-15. SERS intensity was high when P. falciparum wildtype target sequences were added, owing to the complementarity between probe and target sequences. In contrast, after the addition of a P. falciparum mutant sequence, the SERS intensity was low, owing to a single-based pair mismatch which allows the unstable double strands to dehybridize and thereby attenuate SERS intensity. For the non-falciparum sequence and blank, SERS intensities were close to zero. These data demonstrate the feasibility and specificity of SERS nanorattle-based detection of P. falciparum gene targets.

Figures 14A, 14B:
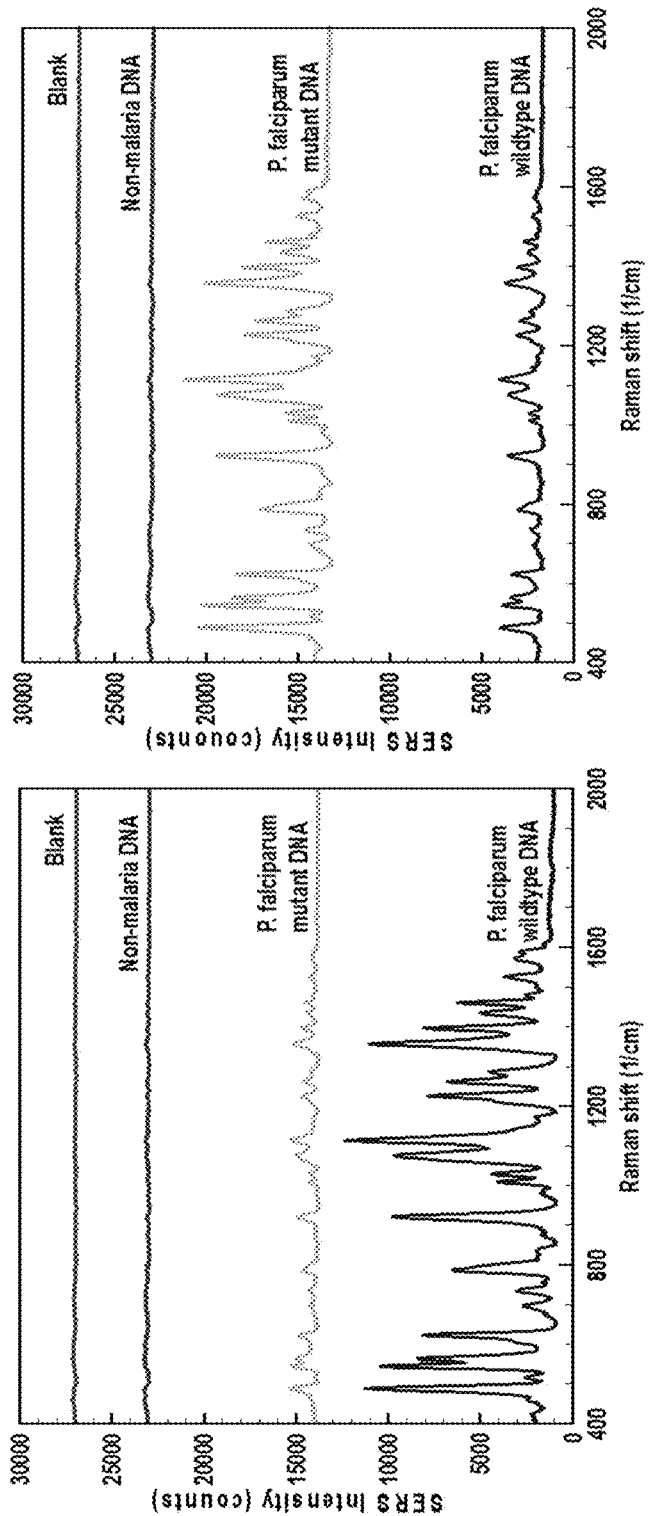
FIG. 14A shows detection of wild type P. falciparum and mutant P. falciparum with a single nucleotide difference using the nanorattle-based method (vertically shifted for clarity). Two probes, one for wild type P. falciparum (a) and one for mutant P. falciparum (b), were designed and tested against P. falciparum wild type DNA, P. falciparum mutant DNA, non-malaria DNA, and blank. The wild type DNA and the mutant DNA have a single base difference and is a graph showing SERS intensity emitted from a reporter complementary to the wildtype sequence measured after addition of wildtype oligo (P. falciparum wildtype DNA), single-base mismatch oligo (P. falciparum mutant DNA), non-falciparum oligo (Non-malaria DNA), and buffer (Blank).
FIG. 14B shows detection of wild type P. falciparum and mutant P. falciparum with a single nucleotide difference using the nanorattle-based method (vertically shifted for clarity). Two probes, one for wild type P. falciparum (a) and one for mutant P. falciparum (b), were designed and tested against P. falciparum wild type DNA, P. falciparum mutant DNA, non-malaria DNA, and blank. The wild type DNA and the mutant DNA have a single base difference and is a graph showing SERS intensity emitted from a reporter complementary to the mutant single-base mismatch sequence measured after addition of wildtype oligo (P. falciparum wildtype DNA), single-base mismatch oligo (P. falciparum mutant DNA), non-falciparum oligo (Non-malaria DNA), and buffer (Blank).

Detection of wild type P. falciparum and mutant P. falciparum with a single nucleotide difference using the nanorattle-based method is shown in FIG. 14 (vertically shifted for clarity). Two probes, one for wild type P. falciparum (a) and one for mutant P. falciparum (b), were designed and tested against P. falciparum wild type DNA, P. falciparum mutant DNA, non-malaria DNA, and blank. The wild type DNA and the mutant DNA have a single base difference. SNP discrimination using SERS has been previously reported. To demonstrate the SNP discrimination capability of the nanorattle-based method, wild type and mutant DNA sequences of the malaria parasite P. falciparum gene PF3D7_1343700 ("K13") were used as models. 53nt K13 sequences were tested with ("Mut") and without ("WT") a SNP encoding the C580Y substitution that confers resistance to Art-R. Based on the two sequences, referred to as target sequences, reporter probes for P. falciparum WT and of P. falciparum Mut were designed. A common capture probe for the two target sequences was also designed. Samples containing P. falciparum WT target sequence, P. falciparum Mut target sequence, a non-malaria sequence, or buffer only were tested against the two reporter probes in parallel as described in the experimental section. The results are shown in FIG. 14. Both WT reporter probe and Mut reporter probe can specifically detect WT target sequence and Mut target sequence, respectively. For the WT reporter probe (FIG. 14A), the SERS intensity was high in the presence of P. falciparum WT target sequences. This is due to the perfect matching between the WT reporter probes and the WT target sequences, resulting in stable double strands. More nanorattles could then attach to the magnetic beads via sandwich formation, thus resulting in high SERS intensity. However, in the presence of P. falciparum Mut target sequences, the SERS intensity was low (FIG. 14B). This is due to the single-base mismatch between the WT reporter probes and the Mut target sequences, resulting in less stable double strands. With the stringent washing step using low-salt washing buffer at 37° C., these unstable double strands will dehybridize. A lower number of nanorattles were attached to the magnetic beads, resulting in low SERS intensity. For non-malaria sequence and blank, SERS intensities were close to zero (FIG. 14A), indicating that non-specific hybridization and undesired adsorption were marginal. By dividing SERS peak intensity at 923 cm$^{-1}$ of WT probe-WT target by that of WT probe-Mut target, a SNP discrimination ratio was obtained of approximately 8:1 for the WT probe. Similarly, for the Mut reporter probe (FIG. 14B), SERS intensity was high in the presence of $P.$ $falciparum$ Mut target sequences and low in the presence of $P.$ $falciparum$ WT sequences. SERS intensities were close to zero for both non-malaria sequences and blank. By dividing the SERS peak intensity at 923 cm$^{-1}$ of Mut probe-Mut target by that of Mut probe-WT target, the SNP discrimination ratio was determined to be approximately 3.2:1 for the Mut probe. The results clearly demonstrate the SNP discrimination capability of the nanorattle-based method.

It is noteworthy that conditions of the stringent washing step, including temperature and salt concentration, are crucial to the SNP discrimination experiment's success. To investigate the effect of temperature of the stringent washing step, the SNP discrimination experiment was repeated except that the stringent washing step was conducted at room temperature as opposed to 37° C. The results show that the discrimination capacity was adversely affected. While the WT probe can still discriminate between WT target and Mut target but at lower discrimination ratio 2.5:1, the Mut probe couldn't discriminate between Mut target and WT target. Choosing an appropriate temperature for the stringent washing step is therefore important to SNP discrimination success. Generally, this can be achieved via determining melting temperatures of perfectly-matched double strand and of single-base mismatched double strand in combination with trial-and-error. The use of two reporter probes, WT probe and Mut probe, is effective for not only SNP discrimination but also for target composition identification.

The formation of hybridization sandwiches of magnetic bead-target sequence-nanorattle was verified by SEM images (data not shown). In the presence of complementary target sequences, nanorattles were bound onto magnetic beads' surface. In contrast, in the absence of complementary target sequences (i.e. buffer only), almost no nanorattle was found. The result indicated that hybridization sandwiches of (1) magnetic beads loaded with capture probes, (2) target sequence, and (3) nanorattles loaded with reporter probes successfully formed in the presence of complementary target sequences. As the magnetic beads (ca. 1 μm diameter) were much bigger than the nanorattles (ca. 60 nm diameter), tens of nanorattles were found on each magnetic bead.

In addition, the sensitivity of the nanorattle-based technique was quantified by testing samples of the $P.$ $falciparum$ wildtype target sequence at different concentrations. Quantification results are shown in FIG. 15. As shown in FIG. 15A, SERS intensity decreases when target concentration decreases, suggesting that a lower number of magnetic bead-target sequence-nanorattle sandwiches were formed at lower target concentration. SERS peak intensities at 923 cm$^{-1}$ of different concentrations in FIG. 15A were normalized against the 923 cm$^{-1}$ peak intensity of the highest concentration, i.e. 100 pM, and plotted in FIG. 15B. From the results, the limit of detection was determined to be approximately 3 picomolar ($3\times10^{-12}$ M). Since the sample solutions' volumes were 30 μL, at 3 picomolar concentration, the copy number of target sequences was below 100 attomoles ($10^{-16}$ moles). It is noteworthy that for sample solutions at 1 nM concentration detector saturation was observed due to strong SERS signals. The linear range of this method is therefore expected to be between $10^{-11}$ M to $10^{-10}$ M target concentration. For detection at higher target concentrations without detector saturation, a shorter detector's exposure time can be used.

The results indicated that the current unoptimized nanorattle-based technique could detect malaria ($P.$ $falciparum$ wildtype target sequence) at 100 femtomolar concentration range. By considering the signal-to-noise ratio values, the limit of optical detection (LOD) is estimated at 10 femtomolar concentration even without having optimized the experimental conditions. Since only 20 μL samples were used, the absolute LOD is 200 zeptomoles ($2\times10^{-19}$ moles) of the malaria target.

In another assay an 80-nucleotide specific sequence within the 3' untranslated region (UTR) of DENV1 (GenBank JQ692085.1) was targeted with gene capture and gene reporter probes using the Nanoratle-based technique. The DENV1 target sequence was tested at concentrations of 10 nM, 1 nM, 100 pM, 10 pM, 1 nM, and 100 femtomolar (data not shown). The SERS signal could still be detected at 100 femtomolar concentration of DENV1 target sequence. This sensitivity is similar to that achieved in preliminary $P.$ $falciparum$ detection with an LOD at 200 zeptomoles ($2\times10^{-19}$ moles). By targeting different specific sequences of four different DENV serotypes, this method can be used for detection, quantification, and serotyping of DENV.

Any patents or publications mentioned in this specification are indicative of the levels of those skilled in the art to which the invention pertains. These patents and publications are herein incorporated by reference to the same extent as if each individual publication was specifically and individually indicated to be incorporated by reference. In case of conflict, the present specification, including definitions, will control.

One skilled in the art will readily appreciate that the present invention is well adapted to carry out the objects and obtain the ends and advantages mentioned, as well as those inherent therein. The present disclosure described herein are presently representative of preferred embodiments, are exemplary, and are not intended as limitations on the scope of the invention. Changes therein and other uses will occur to those skilled in the art which are encompassed within the spirit of the invention as defined by the scope of the claims.

We claim:

1. A method of making tunable Reporter loaded SERS nanorattles comprising:

contacting gold nanoparticle (AuNP) seed with silver (Ag) to form an essentially uniform width Ag shell surrounding the AuNP nanoparticle seed core thereby forming a AuNP-core/Ag-shell structure (AuNP@Ag), wherein the essentially uniform width of the Ag shell is tunable;

forming pores in the Ag shell of the AuNP@Ag through galvanic replacement between Ag and AuCl$_4^-$, thereby forming an AuNP-core/Ag-cage structure (AuNP@Cage) having a porous shell of essentially uniform width;

contacting the AuNP@Cage with a phase-change material and one or more reporter molecules to form a reporter-loaded AuNP-core/Ag-cage structure (Reporter loaded AuNP@Cage), whereby the one or more reporter molecules are loaded in the pores of the porous shell such that the porous shell serves as a sacrificial template for loading of the one or more reporter molecules; and contacting the Reporter loaded AuNP@Cage with Au thereby forming an Au shell encapsulating the Reporter loaded AuNP@Cage, wherein the formed structure is a nanorattle (Reporter loaded SERS nanorattle), and wherein in the nanorattle, the gold nanoparticle seed serves as the Au nanoparticle core, the Au encapsulating shell serves as the shell of the nanorattle and the sacrificial template of the porous Ag shell provides an essentially uniform gap between the Au nanoparticle core and Au encapsulating shell for loading of the one or more reporter molecules.

2. The method of claim 1, wherein contacting the AuNP seeds with Ag includes contacting the AuNP seeds with a stabilizing agent.

3. The method of claim 2, wherein the stabilizing agent is polyvinylpyrrolidone (PVP).

4. The method of claim 1, wherein contacting the AuNP seeds with Ag includes contacting the AuNP seeds with a solution of silver nitrate ($AgNO_3$).

5. The method of claim 4, wherein contacting the AuNP seeds with Ag further includes contacting the AuNP seeds with cetyltrimethylammonium chloride (CTAC).

6. The method of claim 4, wherein the essentially uniform width of the Ag shell is tunable through variation of the amount of the AuNP seeds or by variation of the amount of the $AgNO_3$.

7. The method of claim 1, wherein forming pores in the Ag shell of the AuNP@Ag includes modifying the AuNP@Ag in a solution with PVP and contacting the PVP-modified AuNP@Ag solution with a $HAuCl_4$ solution while stirring to form the AuNP@Cage.

8. The method of claim 1, wherein the phase-change material comprises 1-tetradecanol.

9. The method of claim 1, wherein contacting the Reporter loaded AuNP@Cage with Au includes contacting the Reporter loaded AuNP@Cage with a solution of $HAuCl_4$ and addition of an acid.

10. The method of claim 9, wherein the acid is ascorbic acid.

11. The method of claim 1, wherein the reporter is a Raman dye.

12. The method of claim 11, wherein the reporter is one or a combination of 2-[7-(1,3-dihydro-1,3,3-trimethyl-2H-indol-2-ylidene)-1,3,5-heptatrienyl]-1,3,3-trimethyl-3H-indolium iodide (HITC), Methylene Blue, or Rose Bengal.

13. The method of claim 1, wherein an average diameter of the AuNP seeds is approximately 20 nm.

14. The method of claim 1, wherein an average diameter of the Reporter loaded SERS nanorattle is approximately 50-60 nm.

15. The method of claim 1, wherein an average diameter of the Reporter loaded SERS nanorattle ranges from about 30-110 nm.

16. The method of claim 1, wherein the width of the essentially uniform gap between the Au nanoparticle core and Au encapsulating shell of the Reporter loaded SERS nanorattle Reporter is 2 nm, 5 nm, or 10 nm.

* * * * *